United States Patent
Jordan et al.

(10) Patent No.: US 11,375,693 B2
(45) Date of Patent: Jul. 5, 2022

(54) DATA MANAGEMENT SYSTEMS AND METHODS

(71) Applicant: Unified Information Devices, Inc., Lake Villa, IL (US)

(72) Inventors: Craig Jordan, Lake Villa, WI (US); Matthew Ruiter, Deerfield, IL (US); Mitchell Polifka, Wauconda, IL (US)

(73) Assignee: UNIFIED INFORMATION DEVICES, INC., Wilmington, DE (US)

( * ) Notice: Subject to any disclaimer, the term of this patent is extended or adjusted under 35 U.S.C. 154(b) by 546 days.

(21) Appl. No.: 14/929,823

(22) Filed: Nov. 2, 2015

(65) Prior Publication Data
US 2017/0124264 A1 May 4, 2017

(51) Int. Cl.
*A01K 11/00* (2006.01)
*G06K 19/07* (2006.01)
(Continued)

(52) U.S. Cl.
CPC .......... *A01K 11/006* (2013.01); *A01K 11/005* (2013.01); *A01K 29/005* (2013.01);
(Continued)

(58) Field of Classification Search
CPC ........ G16H 10/40; G16H 10/60; G16H 40/20; A01K 11/006; A01K 29/005; A01K 29/00; A01K 11/004; A01K 15/02
(Continued)

(56) References Cited

U.S. PATENT DOCUMENTS

2009/0234275 A1* 9/2009 Jacobson .............. A61M 5/142
   604/31
2012/0193415 A1* 8/2012 Coiro, Sr. .............. A01K 1/031
   235/385

(Continued)

FOREIGN PATENT DOCUMENTS

| CN | 102919142 A * | 2/2013 | |
| EP | 2147399 B1 * | 8/2015 | ........... G06Q 20/308 |
| WO | WO-2006034165 A2 * | 3/2006 | ......... G06F 19/3456 |

OTHER PUBLICATIONS

Chao-Hsi Huang, Pin-Yin Shen and Yueh-Cheng Huang, "IoT-based physiological and environmental monitoring system in animal shelter," 2015 Seventh International Conference on Ubiquitous and Future Networks, 2015, pp. 317-322, doi: 10.1109/ICUFN.2015.7182557 (Year: 2015).*

*Primary Examiner* — Hiep V Nguyen
(74) *Attorney, Agent, or Firm* — Locke Lord LLP; Kathleen J. Swan; Christopher J. Capelli

(57) ABSTRACT

A system for integrating at least one object with an animal within a research facility comprises at least one animal within the research facility, the at least one animal having a first tag associated therewith that is configured to communicate with a data management system. The system further includes at least one laboratory object having a second tag associated therewith and being associated with the at least one animal, the second tag being configured to communicate with the data management system. Still further, the system includes at least one technician badge having a third tag associated therewith, the badge configured to communicate with the data management system. The at least one animal, the at least one laboratory object, and the at least one technician badge are configured to transmit information to the data management system.

12 Claims, 15 Drawing Sheets

(51) Int. Cl.
　　　*G16H 40/20*　　　(2018.01)
　　　*A01K 29/00*　　　(2006.01)
　　　*G06K 19/077*　　(2006.01)
　　　*G16H 10/40*　　　(2018.01)

(52) U.S. Cl.
　　　CPC ... *G06K 19/0723* (2013.01); *G06K 19/07758* (2013.01); *G16H 10/40* (2018.01); *G16H 40/20* (2018.01)

(58) Field of Classification Search
　　　USPC .............................................................. 705/2
　　　See application file for complete search history.

(56) References Cited

U.S. PATENT DOCUMENTS

| | | | | |
|---|---|---|---|---|
| 2012/0265702 | A1* | 10/2012 | Maher | G06Q 10/10 705/317 |
| 2013/0113622 | A1* | 5/2013 | Pratt | G06Q 10/0833 340/539.13 |
| 2014/0123906 | A1* | 5/2014 | Conger | A01K 1/0047 119/416 |

* cited by examiner

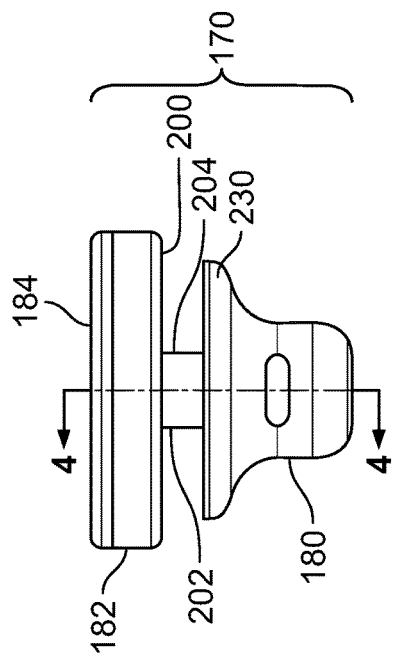
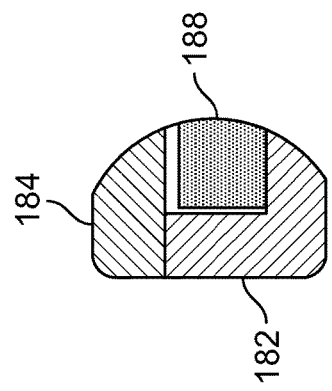
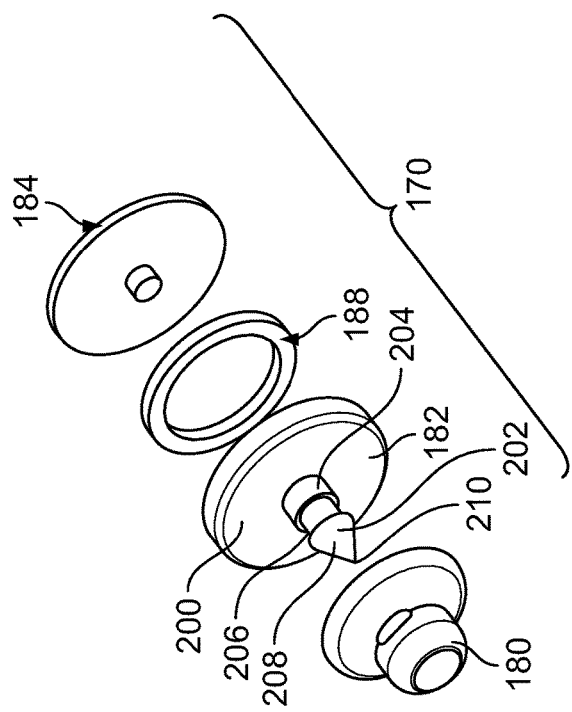
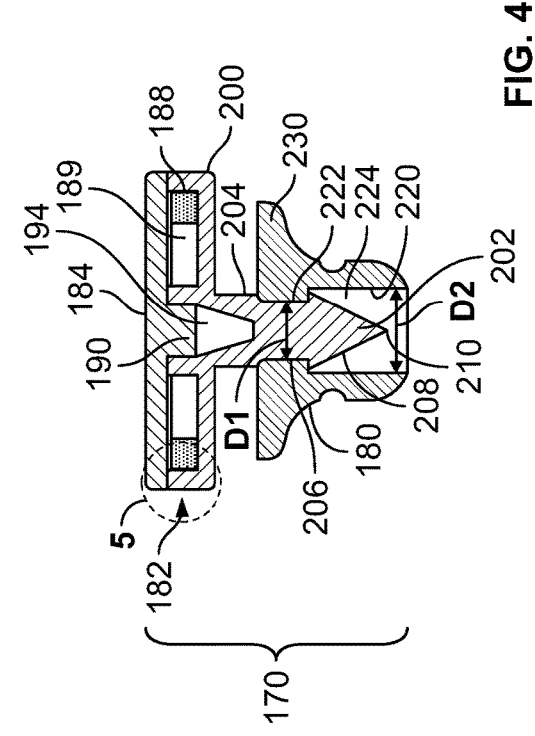

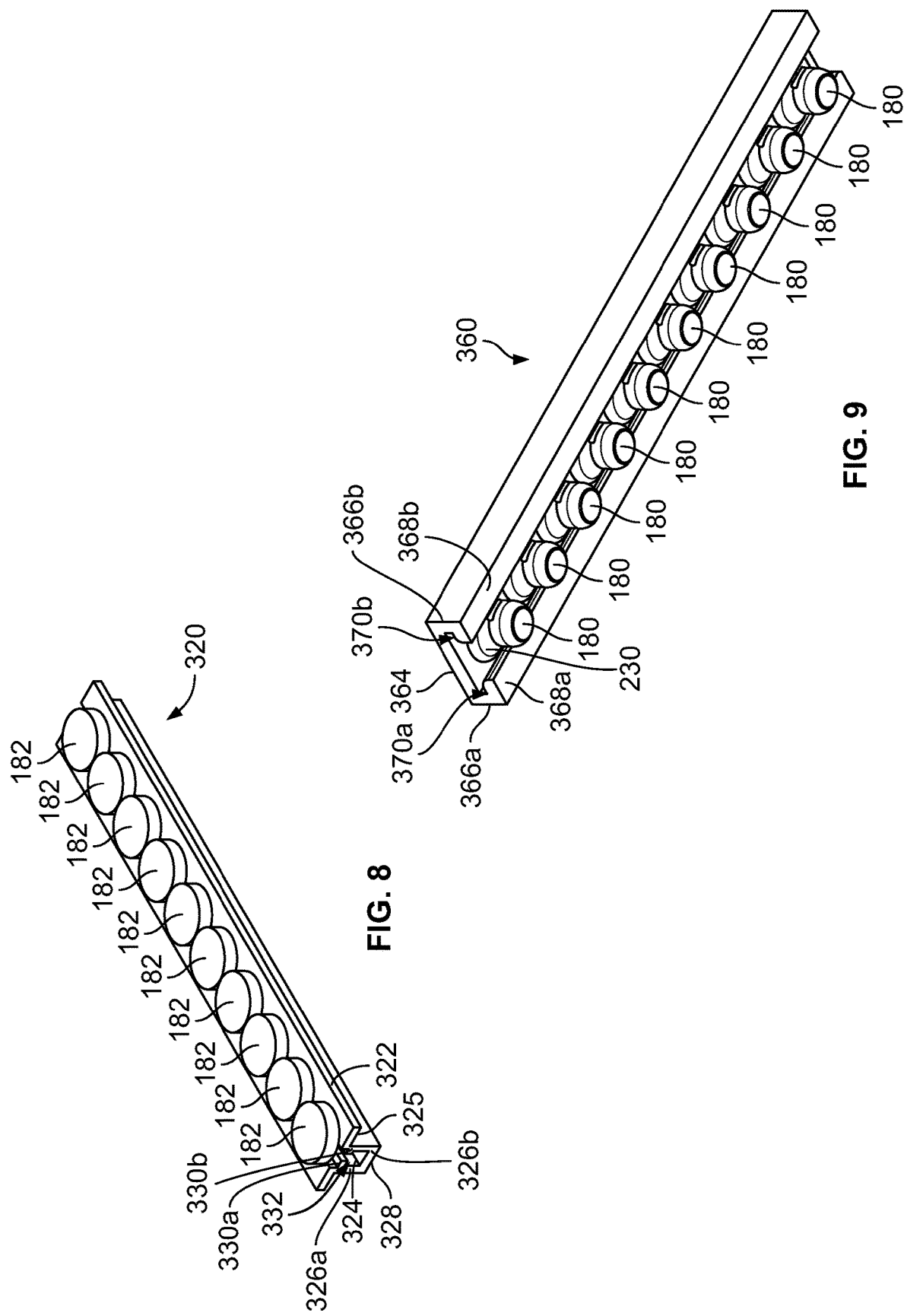

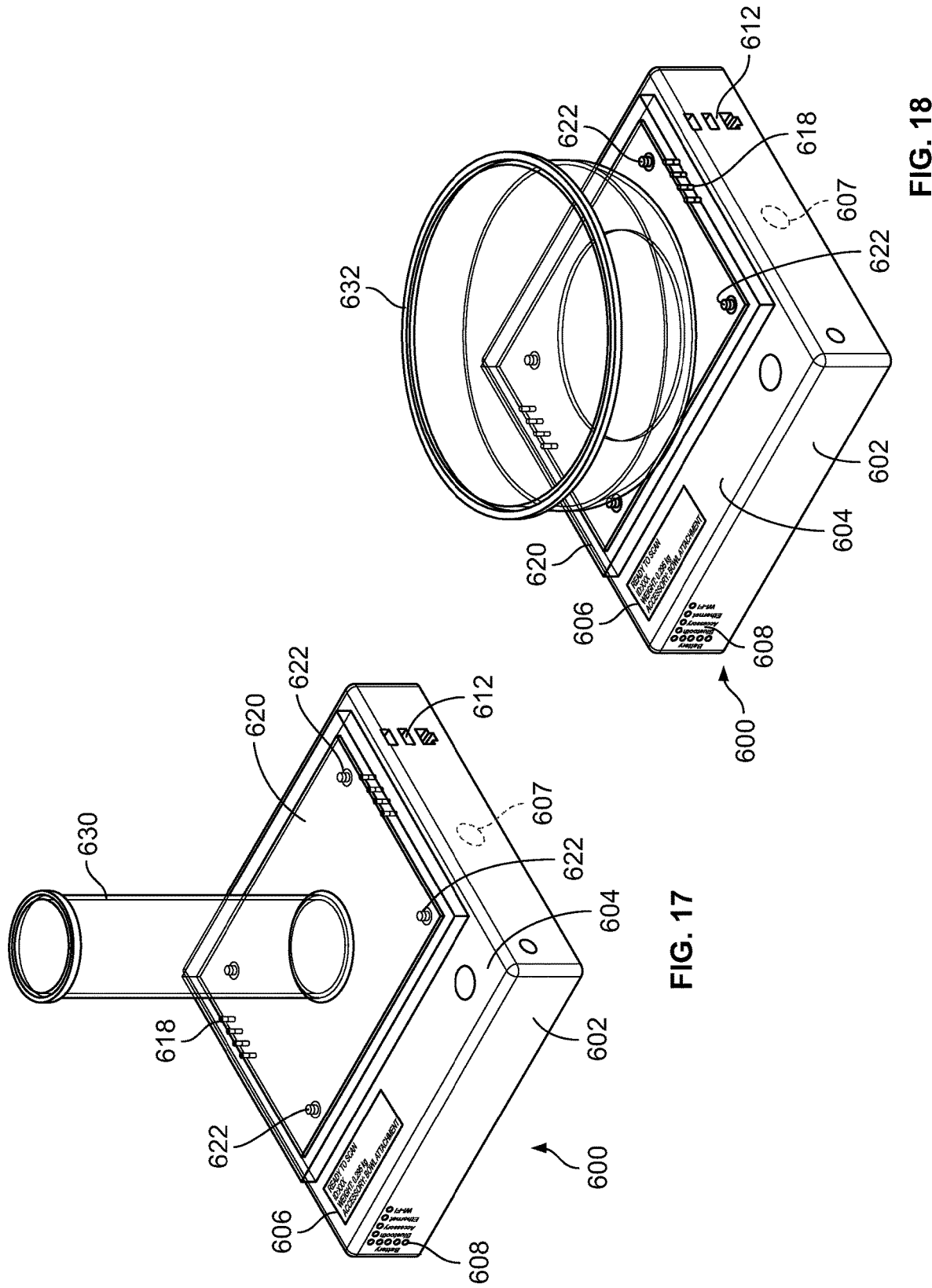

DATA MANAGEMENT SYSTEMS AND METHODS

BACKGROUND

Animals such as mice are often used to conduct research. For example, animals may be injected with predetermined doses of a drug or drugs to enable a researcher to study the effects of the drug(s) on the animals. The animals are typically provided with visual indicators that indicate the respective animals' identification to enable the researcher or a technician to distinguish the identity of one animal in a cage or other container from the other animals. For example, each of the animals may be tattooed with a unique symbol or number.

To conduct a study in a research facility, technicians must perform actions, such as, for example, locating and identifying an animal in a cage, removing the animal from the cage, measuring characteristics of the animal, injecting the animal with drugs or conducting other tests on the animal, returning the animal to the cage, and/or other actions. In studies utilizing small animals, for example, rodents such as mice or rats, a technician oftentimes has difficulty locating the proper animal for study. More particularly, multiple, oftentimes dozens, of rodents may be kept in the same cage or other container and, upon opening of the cage, the rodents scurry around the cage, which makes it difficult to locate the correct rodent. The technician must remove a rodent, check the identification, and, if the rodent is not the correct rodent, replace the rodent. This process must be repeated until the correct rodent is located, which can be very time consuming.

Data collection and authentication in a research environment are also important to validate results. Frequently, data collection in a research facility involves the technician following multiple steps in a certain order, and documenting specific results. In many cases, steps may be missed and/or results are documented improperly or lost. Not only are these procedures time consuming, they may also introduce error. As is apparent, current research facility systems and procedures can be very inefficient, time consuming, and error prone. It is therefore desirable to improve research facility systems and procedures.

SUMMARY

In illustrative embodiments, a system for integrating at least one laboratory object with an animal within a research facility that may comprise at least one animal within the research facility, the at least one animal having a first tag associated therewith that is configured to communicate with a data management system. The system may further include at least one laboratory object having a second tag associated therewith and being associated with the at least one animal, the second tag being configured to communicate with the data management system. Still further, the system may include at least one technician badge having a third tag associated therewith, the badge configured to communicate with the data management system. The at least one animal, the at least one laboratory object, and the at least one technician badge may be configured to transmit information to the data management system.

In other illustrative embodiments, a stapler for attaching a tag to an animal may comprise first and second arms pivotally connected to one another, a first cartridge attached to the first and containing a plurality of male tag components, and a second cartridge attached to the second arm and containing a plurality of female tag components.

In further illustrative embodiments, a provisioning station for programming at least two tags associated with animals or objects within a research facility may comprise at least two stations each configured to hold a tag for programming. The provisioning station may further include a tag programmer configured to send information to each tag disposed within the at least two stations for storage of the information on the respective tags and a controller configured to transmit information related to actions undertaken by the controller and information transmitted to the tags to a data management system.

In still other illustrative embodiments, a tag for attachment to an ear of a rodent may comprise a male coupling including a housing and a spike extending outwardly from the housing, wherein a radio-frequency identification (RFID) chip is disposed within the housing and programmed to include a unique identification number for a rodent to which the tag is attached. The tag may further include a female coupling including a channel for accepting and retaining the spike of the male coupling. The tag may further include first visual indicator that identifies a first characteristic of the rodent to which it is attached and a second visual indicator that identifies a second characteristic of the rodent to which it is attached, the first and second characteristics being different from one another and being different than the unique identification number for the rodent.

In other illustrative embodiments, a computer-implemented method for integrating at least one laboratory object with an animal within a research facility may include the step of receiving at a data management system a first unique identifier associated with an animal within the research facility, wherein the first unique identifier is obtained by scanning a first tag associated with the animal. The method may further include the step of receiving at the data management system information associated with a laboratory object within the research facility, wherein the information includes information identifying the specific laboratory object, wherein the information is obtained by scanning a second tag associated with the laboratory object. Still further, the method may include the steps of receiving at the data management system a second unique identifier associated with a technician within the research facility, wherein the second unique identifier is obtained by scanning a badge associated with the technician and determining whether the information associated with the laboratory object is associated with the first unique identifier and if the laboratory object is associated with the first unique identifier, prompting the technician to undertake a particular action.

DESCRIPTION OF THE DRAWINGS

FIG. 2 is an exploded view of an exemplary tag that may be associated with an animal, for example, in the research facility system of FIG. 1;

FIG. 3 is a side elevational view of the tag of FIG. 2 in an assembled condition;

FIG. 4 is cross-sectional view of the tag of FIG. 2 taken generally along the lines 4-4 of FIG. 3 and depicting an assembly of the tag;

FIG. 5 is an enlarged close-up view of a portion of the tag indicated by the circled portion labeled (5) in FIG. 4;

FIG. 8 is a perspective view of a first cartridge holding a plurality of male couplings forming the tag of FIGS. 2-5 and for use with the stapler of FIGS. 7 and 8;

FIG. 9 is a perspective view of a second cartridge holding a plurality of female couplings forming the tag of FIGS. 2-5 and for use with the stapler of FIGS. 7 and 8;

FIGS. 16-18 are to perspective views of the scale of FIG. 15 with various accessories mounted or placed thereon;

DETAILED DESCRIPTION

Figure 1:
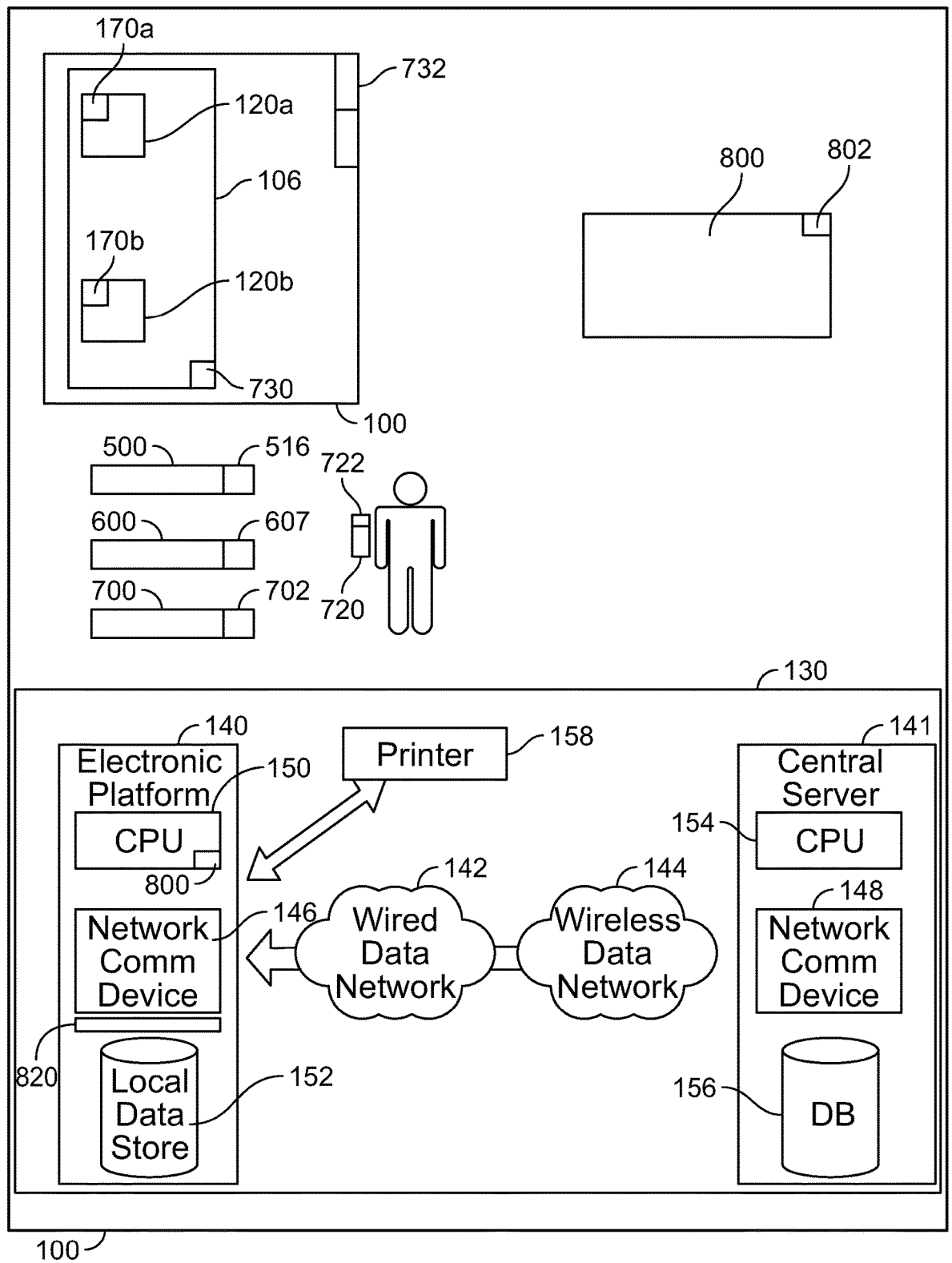
FIG. 1 is a schematic view depicting a research facility system according to some aspects of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

The following detailed description is to be read with reference to the figures, in which like elements in different figures have like reference numerals. The figures, which are not to scale, depict examples of apparatuses, methods, and systems for use in a research facility and in accordance with the teachings of this disclosure.

In some research studies involving animals, the animals are periodically injected with drugs to enable researchers to study the effects of the drugs on the animals. To conduct the study, a technician performs actions such as, for example, locating and identifying an animal in a cage, removing the animal from the cage, measuring characteristics of the animal, injecting the animal with a predetermined dose of the drug, returning the animal to the cage, and/or one or more additional and/or different actions. Example apparatuses, methods, and systems disclosed herein automatically collect and organize information related to the technician's actions in a database when the technician is performing the actions and integrate various apparatuses, methods, and systems within the research facility to make research procedures more efficient.

FIG. 1 illustrates an example research facility system 100 in which the apparatuses, methods, and systems of the present invention may be implemented. In the illustrated example, the research facility 100 is a laboratory. In other examples, the research facility may be any other type of research facility. The research facility 100 of FIG. 1 includes equipment and/or supplies such as, for example, a rack 104, one or more animal cages 106 supported on the rack 104, one or more syringes 700, one or more scales 600, tongs 500 for holding an animal 120, badges or identification cards 720 associated with laboratory technicians, and/or other laboratory object. Laboratory object may include any equipment, devices, and/or supplies, for example, a scale, a dosing apparatus, a pump, a syringe, a label, a microscope slide, a pipette, a needle, a box, a tissue cassette, a bottle, calipers, a vial, a beaker, a cage, a rack, or any other object within a laboratory. A first animal 120a and a second animal 120b (e.g., mice or rats) may be housed in the cage 106 of FIG. 1. In other examples, other numbers (e.g., 1, 3, 4, 5, . . . 50, etc.) of animals 120 may be housed in the cage 106.

In the illustrated example, the research facility system 100 may include a data management system 130 that collects, organizes, analyzes, and/or processes information related to laboratory objects and/or animals 120, and/or actions taken within the research facility 100, etc. The system 130 enables communication between one or more electronic platforms 140, for example, a desktop computer, a laptop computer, a tablet, a mobile device, or any other suitable electronic platform, one or more central servers 141, and any number of tags (e.g., radio frequency identification tags) associated with any number of animals and/or laboratory objects. While the central server 141 is shown as being within the research facility 100, one or more central servers 141 may be additionally or alternatively located remote from the research facility 100. The system 130 may include any number of electronic platforms 140 connected through a wired data network 142 and/or a wireless data network 144 to each other and/or the central server(s) 141. The wired data network 142, if present, may be coupled to the wired data network 144 and may be a global network, a wide area network, or a local area network. The wireless data network 144, if present, may be coupled to the wired data network 142 and may include one or more wireless data networks, such as cellular networks, WiFi networks, Bluetooth networks, etc. The electronic platforms 140 and/or the central server(s) 141 may be coupled to one or both of the wired data network 142 and the wireless data network 144 through a network communication device 146 within the electronic platform 140 and a network communication device 148 within the central server(s) 141. In an illustrative embodiment, the electronic platforms 140 may couple to the wired data network 142 over wired connections and to the wireless data network 144 over wireless links. In this manner, the electronic platforms 140 may access the central server(s) 141 through the wired data network 142 and/or the wireless data network 144. Optionally, the central server 141 may be a cloud server or the data management system 130 may additionally include a cloud server.

The electronic platform 140 may include a graphical user interface (not shown) and a computer portion. The graphical user interface may include one or more input/output (I/O) devices, such as a touch screen, a keyboard, a stylus, a joystick, or any other suitable I/O device, which can be arranged in various manners and have different shapes or designs. The touch screen may be a liquid crystal display (LCD), a display screen, a plasma screen, a light emitting diode (LED), or any other screen capable of displaying text and/or images and/or allowing input of text. The computer portion may also include an I/O device, a central processing unit (CPU) 150 (i.e., a microprocessor), memory (not shown), and an optional local data store or database 152. The CPU 150 may be any computer-processing unit, including multi-processor or single processor configurations. The memory 210 generally includes RAM, ROM, flash memory, solid state memory, and/or other persistent or non-transitory computer-readable storage media. The memory may incorporate electronic, magnetic, optical, and/or other types of storage media, and may have a distributed architecture where various components are situated remote form one another, but may still be accessed by the CPU 150, such as cloud computing. The graphical user interface is coupled to the I/O device such that commands or data entered by a user through the graphical user interface will be forwarded to the I/O device, to the CPU 150, and then to the memory. The CPU 150 may include one or more microprocessors configured to communication with the memory to implement a software application 820, as described below, and associated program instructions stored therein.

One or more electronic platforms 140 may be connected, either through the wireless data network 144 or through the wired connection 142 to other electronic platforms 140, the central server 141, and/or to laboratory objects and/or animals 120 (i.e., through communication with a tag associated with the laboratory object or animal) within the system 100, for example, one or more scales 110, or any other apparatuses and/or laboratory objects within the system 100. One or more electronic platforms 140 may additionally or alternatively be connected, either through the wireless data network 144 or through the wired data network 142, to a printer 158. Optionally or additionally, one or more of the electronic platforms 140 may be connected to any other suitable peripheral devices, for example, a camera, a video camera, scanner, plotter, microphone, or any other suitable peripheral device. The one or more electronic platforms 140 may implement software 820, for example, on the CPU 150.

The central server 141 may further include a CPU 154 and a central database 156. The electronic platform 140 communicates via the wired data network 142 and/or the wireless data network 144 with the central server 141 through the network connections 146, 148, to transfer data between the electronic platform 140 and the central server 141. The central server 141 and/or the electronic platform 140 may receive data from one or more radio-frequency identification (RFID) tags disposed within the research facility system 100, as will be discussed in greater detail below. While the term "tag" is utilized throughout the present specification, it should be understood that a tag is any device in any format that is capable of communication with other tags and/or devices throughout the system 100. Still further, while RFID tags are discussed throughout, the present invention is not meant to be limited to RFID communication. For example, optical communication devices, barcodes (either passive or active), or any other suitable communication devices, may be utilized.

While the data management system 130 is depicted as having both an electronic platform or platforms 140 and a central server or servers 141 and the electronic platform or platforms 140 and the central server or servers 141 are depicted as having certain components, one skilled in the art will understand that different implementations are possible. For example, the central server(s) 141 may be eliminated, the electronic platform 140 may not include a local data store, and/or one or more of the databases 152, 156 may be cloud-based, etc.

As will be described throughout the present specification, the data management system 130 collects and stores data (at the electronic platform 140 and/or the central server 141) related to a variety of different tags throughout the research facility system 100. The use of tags, for example RFID tags, throughout the research facility system 100 facilities efficient and accurate data collection. In other embodiments, the tags may utilize any other suitable technology for communication between the tags and/or with the electronic platform 140 and/or central server 141.

The system 100 may include a first set of tags 170 coupled to any number of animals 120 within the research facility system 100. While two animals 120 are depicted in the embodiment of FIG. 1, one skilled in the art would understand that there are usually many more than two animals 120 in a research facility and, oftentimes, hundreds of animals 120. While the systems and methods disclosed herein may be utilized with respect to any type of animal, the systems and methods presented herein are particularly suited for smaller animals, such as rodents (e.g., mice and rats).

Referring to FIG. 1, a first tag 170a is coupled to the first animal 120a. The first tag 170a may be, for example, an RFID tag. The first tag 170a receives, stores, and/or communicates information related to the first animal 120a. For example, the first tag 170a may include identification information (e.g., a unique serial or identification number) assigned to the first animal 120a, attributes (e.g., color, size, sex, etc.) of the first animal 120a, a study number associated with the first animal 120a, a study name associated with first animal 120a, a group number associated with the first animal 120a (e.g., animal group 3), information related to experiments conducted on the first animal 120a (e.g., a name of a drug injected into the first animal, a dosage of the drug injected into the first animal, a concentration of the drug injected into the first animal, one or more timestamps indicating times at which the first animal was injected with the drug, etc.), information about characteristics of the first animal 120a (e.g., species, age, weight, size, behavior, etc.), measured data (e.g., data, such as weight, or characteristics measured at time intervals), and/or any other suitable additional and/or different information.

Still referring to FIG. 1, a second tag 170b is coupled to the second animal 120b. The second tag 170b may be an RFID tag. The second tag 170b receives, stores, and/or communicates information related to the second animal 120b. For example, the second tag 170b may include identification information (e.g., a unique serial or identification number) assigned to the second animal 120b, attributes (e.g., color, size, sex, etc.) of the second animal 120b, a study number associated with the second animal 120b, a study name associated with second animal 120b, a group number associated with the second animal 120b (e.g., animal group 3), information related to experiments conducted on the second animal 120b (e.g., a name of a drug injected into the second animal 120b, a dosage of the drug injected into the second animal, a concentration of the drug injected into the second animal, one or more timestamps indicating times and/or dates at which the second animal was injected with the drug, etc.), information about characteristics of the second animal 120b (e.g., species, age, weight, size, behavior, etc.), measured data (e.g., data, such as weight, or characteristic measured at time intervals) and/or additional and/or different information. Similarly, any other additional animals 120 may include respective tags 170 with the same or different information. Dependent upon a particular study, result, or methodology, different information may be received, stored, and/or communicated by a particular tag 170.

In a non-limiting exemplary embodiment, each tag 170 may include identifying information, for example, a unique identification code for the particular animal. In some embodiments, one or more tags 170 may additionally include a visual indicator, such as a color and/or a number, which indicate particular characteristics of the animal 120. The technician may use the information related to the visual indicator to initially identify and remove the animal 120 in the cage 106 and may further use one or more of the devices disclosed herein to further confirm the identity of the animal 120. In an exemplary embodiment, a tag 170 may, in addition to the RFID identifier, be colored a particular color, which indicates a first characteristic of the animal 120, for example, a breed, a study, or any other characteristic, and the tag 170 may include a number, which indicates, for example, an identification number for the animal 120.

As noted above, the tags 170 are RFID tags that are capable of communicating with various apparatuses and/or laboratory objects within the research facility system 100, as will be discussed in greater detail below. The tags 170 are physical tags that are attached to, for example, an ear of the animal 120. FIGS. 2-5 depict an exemplary embodiment of a tag 170 for use in the systems and methods of the present specification. In the illustrated example, the tag 170 includes a female coupling 180, a male coupling 182 configured to engage and be retained within the female coupling 182, a cover 184 coupled to a side of the male coupling 182 opposite the female coupling 180, and an E-coil 188 disposed within an annular cavity 189 formed between the cover 184 and the male coupling 182 and, as best seen in FIG. 3, is not compressed between the cover 184 and the male coupling 182. The E-coil 188 includes an antenna and a microchip for communication with other tags in the research facility system 100. The E-coil 188 may be epoxied, glued, welded, or potted into the cavity 189 within the male coupling 182. As seen in FIG. 4, the cover 184 may include a projection 190 that extends outwardly therefrom to engage a cavity 194 within the male coupling 182 to secure (e.g., by snap fit) the cover 184 to the male coupling 182. In other embodiments, the cover 184 may be coupled to the male coupling 182 in any other suitable manner. In some embodiments, a seal between the cover 184 and the male coupling 182 is water tight and tamper proof.

As seen in FIGS. 2 and 4, the male coupling 182 includes a housing 200 and spike 202 extending outwardly from the housing 200. The spike 202 includes a shoulder 204 extending from the housing 200, a neck 206 extending from the shoulder 204 and having a lesser diameter than the shoulder 204, and a conical head 208 extending from the neck 206 and having a widest diameter adjacent the neck 206, which is greater than the diameter than the neck 206. A distal end 210 of the head 208 terminates in a point. As described in greater detail below, the distal end 210 of the head 208 pierces the ear of an animal when the male coupling 182 is coupled to a female coupling 180.

The female coupling 180 includes an aperture or channel 220, as best seen in FIG. 4, to receive a portion of the spike 202 (e.g., the neck 206 and/or the head 208). The channel 220 includes a first portion 222 having a first diameter D1, and a second portion 224 having a second diameter D2 greater than the first diameter D1. In an exemplary embodiment, the second portion 224 of the channel 220 may be a counter bore. In some exemplary embodiments, the female coupling 180 may be elastically deformable to enable the first portion 222 of the channel 220 to expand as the head 208 of the spike 202 moves through the first portion 222 of the channel 220. Once the head 208 moves into the second portion 224 of the channel 220, the first portion 222 of the channel 220 contracts and engages the neck 206 of the spike 202 to secure (e.g., snap-fit) the male coupling 182 to the female coupling 180 (i.e., with the first portion 22 of the female coupling 180 within the neck 206 of the male coupling 182). In the illustrated example, the female coupling 180 includes a collar 230.

While the tag 170 is shown as having a generally circular profile, other profiles are possible, for example, square shaped, triangular, oval, polygonal, or any other suitable shape. In exemplary embodiments, a width f the tag 170 is between about 4 and about 12 millimeters, or between about 5 and about 8 millimeters, or about 6 millimeters.

Referring to FIG. 3, when the male coupling 182 is coupled to the female coupling 180, the housing 200 of the male coupling 182 is spaced apart from the female coupling 180 to enable an ear of the animal 120 to be disposed between the female coupling 180 and the housing 200. Thus, when the tag 170 is coupled to the animal 120, the housing 200 is disposed on a first side of the ear, the female coupling is disposed on a second side of the ear opposite the first side, and a first portion (e.g., the shoulder 204) of the spike 202 is disposed in an aperture pierced in the ear by the spike 202.

Figure 7:
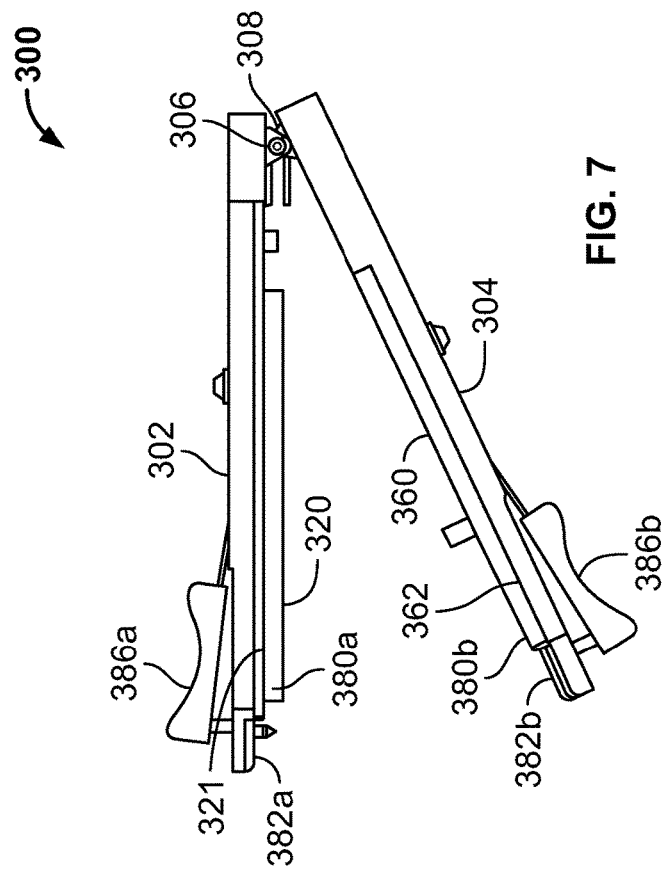
FIG. 7 is a side elevational view of the stapler of FIG. 6 in an assembled condition.
Figure 6:
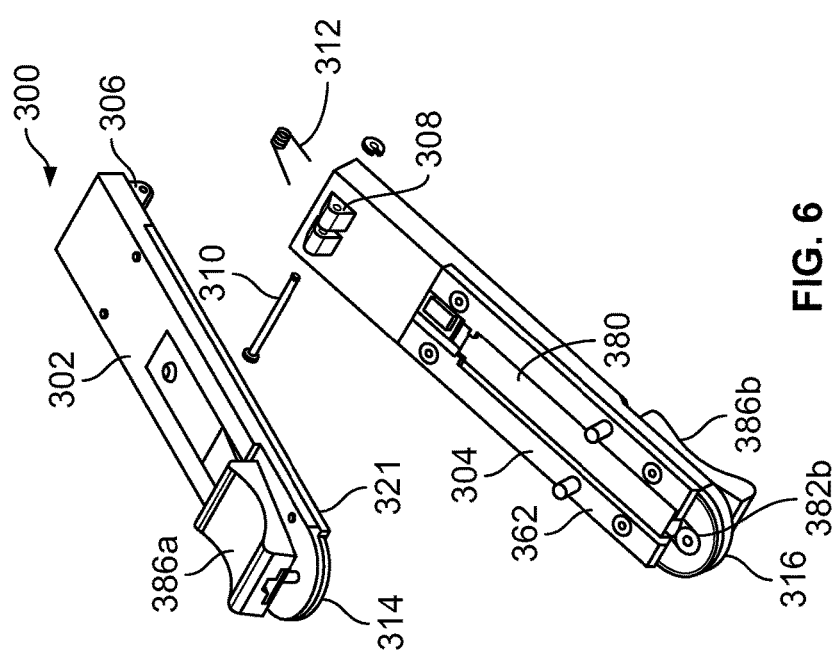
FIG. 6 is an exploded view of a stapler for holding and dispensing portions of the tag of FIGS. 2-5 for attachment to an animal.

The tags 170 may be coupled to the animal 120, for example, using a stapler 300, as seen in FIGS. 6 and 7. The stapler 300 includes first and second arms 302, 304 having first and second fulcrums 306, 308, respectively, at ends thereof. A pin 310 extends through the first and second fulcrums 306, 308 to pivotally couple the first and second arms 302, 304 and define an axis or rotation about which the first and second arms 302, 304 rotate. A spring 312 is coupled to the pin 310 to bias a distal end 314 of the first arm 302 away from a distal end 316 of the second arms 304.

Referring to FIG. 7, which is a side view of the stapler 300 of FIG. 6, a first cartridge 320 is coupled to a platform 321 of the first arm 302. In an exemplary embodiment, the cartridge 320, as shown in FIG. 8, includes a planar wall 322 with a track 324 extending from a surface 325 of the generally planar wall 322. The track 324 is generally U-shaped, includes opposing side walls 326a, 326b that are generally perpendicular to the planar wall 322 and an end wall 328 that connects the opposing side walls 326a, 326b, and further includes inwardly extending projections 330a, 330b, the function of which will be discussed in detail below. The track 324 further includes a cavity 332 formed by the opposing side walls 326a, 326b, the end wall 328, and the projections 330a, 330b and extends along a length of the cartridge 320. In an illustrative embodiment, the first cartridge 320 may be attached to the platform 321 of first arm 302 by, for example, sliding the track 324 into a groove (not shown) formed in the platform 321 of the first arm 302. The first cartridge 320 may be retained within the groove by, for example, a friction fit or in any other suitable manner. Optionally, the cartridge 320 may be attached to the first arm 302 or the platform 321 in any suitable manner. One or more male couplings 182 are slid into the track 324 (before or after attachment of the cartridge 320 to the first platform 321) with the projections 330a, 330b extending into the neck 206 of each male coupling 182 to retain the male couplings 182 within the platform 320.

A second cartridge 360, as seen in FIGS. 7 and 9, is coupled to the second arm 304. In an exemplary embodiment, the cartridge 360 is coupled to a platform 362 of the second arm 304. In an exemplary embodiment, the cartridge 360, as seen in FIG. 9, includes a base wall 364, two side walls 366a, 366b extending generally perpendicular to the base wall 364, and inturned walls 368a, 368b extending inwardly from and generally perpendicular to the side walls 366a, 366b. Two opposing cavities 370a, 370b are formed between the base wall 364, the side walls 366a, 366b, and the inturned walls 368a, 368b. In this manner, one or more female couplings 180 may be slid into the cartridge 360 (before or after attachment of the cartridge 360 to the second platform 362) with the collar 230 of the female coupling 180 being retained within the cavities 370a, 370b. In an illustrative embodiment, the second cartridge 360 may be attached to the platform 360 of the second arm 304 by, for example, sliding the base wall 364 of the cartridge 360 into a groove 380 formed in the platform 362 of the second arm 304. The second cartridge 360 may be retained within the groove 380 by, for example, a friction fit or in any other suitable manner. Optionally, the cartridge 360 may be attached to the second arm 304 or the platform 362 in any suitable manner. Still further, while the cartridges 320, 360 are shown as being attached to the arms 302, 304, the cartridges 320, 360 may alternatively be integral with or formed with the arms 302, 304, respectively.

The stapler 300 further includes cavities 382a, 382b adjacent ends 384a, 384b of each of the cartridges 320, 360, respectively, that accommodate a single male or female coupling 182, 180, respectively, for attachment to an ear of the animal 120. After the cartridges 320, 360 are inserted into respective arms 302, 304, a spring (not shown) in each of the cartridges 320, 360 biases the next male or female coupling 182, 180 into the respective cavity 382a, 382b. During use, the ear of the animal 120 is placed between the arms 302, 304 with the cavities 382a, 382b aligned with a point of insertion. A user grasps the stapler 300, for example, by the arms 302, 304 and presses actuators 386a, 386b, which are connected to the arms 302, 304 and generally biased away from the arms 302, 304, toward one another. Pressure on the actuators 386a, 386b causes projections (not shown) on inner surfaces of the actuators 386a, 386b to push the couplings 182, 180 in the cavities 382a, 382b into engagement with one another. After attachment to the ear of an animal 120, the next coupling 182, 180 is then indexed into the respective cavity 382a, 382b for attachment to another animal.

While the stapler 300 is discussed herein as having platforms 321, 362 to which the cartridges 320, 360, respectively, are attached, the cartridge 320, 360 could be alternatively attached directly to the first and second arms 302, 304, respectively. Still further, the cartridges 320, 360 may be removable attached to the arms 302, 304 or permanently attached to the arms, in which case a user would have to insert slide female and male couplings 180, 182 into the cartridges 360, 320 when empty.

Figure 10:
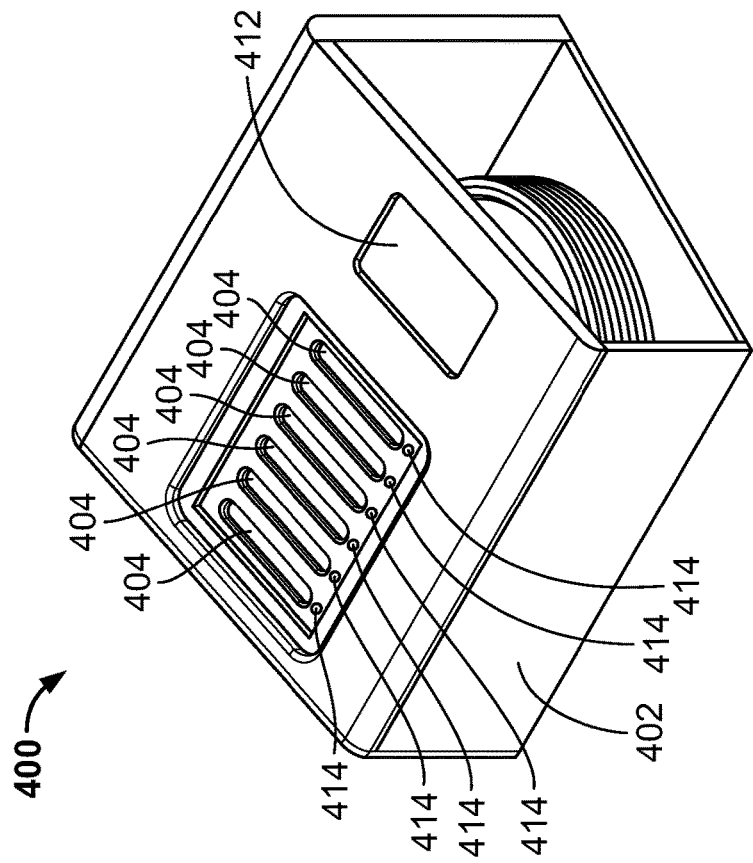
FIG. 10 is a top perspective view of a provisioning station for programming one or more tags and for use within the research facility system of FIG. 1.
Figure 11:
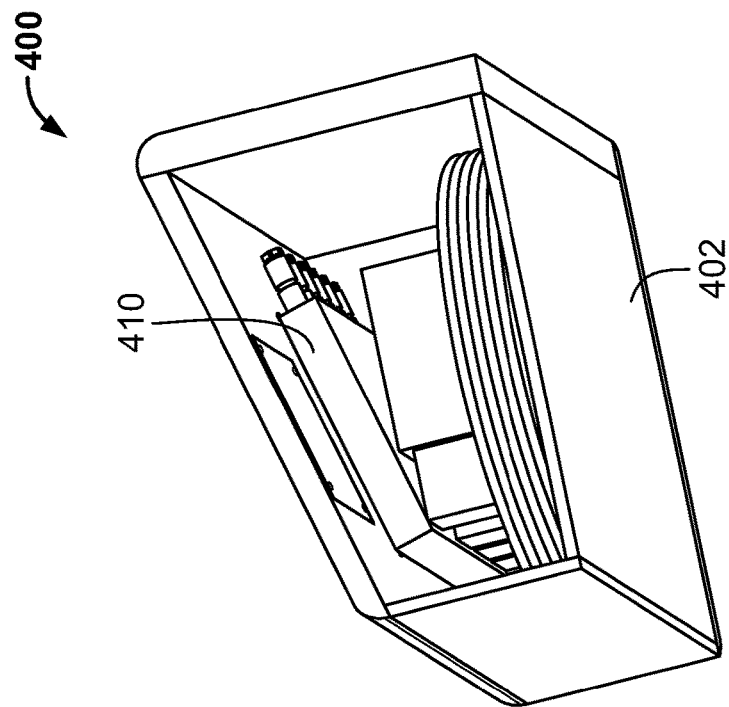
FIG. 11 is a side perspective view of the provisioning station of FIG. 10.

A provisioning station 400, for example, as seen in FIGS. 10 and 11, may be utilized to program one or more tags 170 for one or more animals 120 or any other tag as disclosed herein. The provisioning station 400 generally includes a housing or enclosure 402 having a plurality of stations 404 for placement of one or more tags 170 or any other tags or chips for apparatuses or laboratory objects, for example, for technician badges, vials, microscope slides, syringes, needles, tongs, scales, or any other suitable apparatuses or objects (with one in each station 404). The tags associated with apparatuses or laboratory objects may be similar to those associated with animals 120 or may be different, for example, the tags associated with one or more apparatuses or laboratory objects may be in the form of an embedded chip, a microchip, or any other suitable form. One or more tags are placed within one or more stations 404 in the provisioning station 400 and are simultaneously programmed, for example, to include information and/or data pertaining to the particular animal 120 on which the tag 170 will be placed, as discussed above, or to the apparatus or tag with which the tag is associated. In an exemplary embodiment, the provisioning station 400 may include six stations 404. Six stations 404 provides for simultaneous programming of multiple tags, while maintaining a relatively small profile. More particularly, it is desirous to have a provisioning station 400 that is small, portable, and can be placed on a desktop or other surface within the research facility system 100. In other exemplary embodiments, the provisioning station 400 may include any suitable number of stations 404.

In general, a tag 170 associated with an animal 120 would be placed in the provisioning station 400 prior to attachment to the animal 120 (or if re-programming is needed, the tag 170 would be removed from the animal 120 for programming). Tags associated with apparatuses or laboratory objects may be removed from the apparatus or laboratory object and placed in the provisioning station 400 for programming or the apparatus or object with the tag may be placed within the provisioning station 400. This is important for apparatuses or laboratory objects that need to be sterilized, for example, needles, syringes, etc. In this manner, a syringe for example, does not need to be removed from its sterile packaging for programming.

In some embodiments, the provisioning station 400 may include a tag reader 410 for tracking actions taken, for example, at the provisioning station 400. The tag reader 410 may communicate with the tags disposed within the provisioning station to verify the identity of each tag, collect information about the various tags, record information regarding the programming that takes place, record what technician has performed the programming, and/or any other additional data. The tag reader 410 may also communicate with and/or transmit data to other tags within the system and/or with the data management system 130. The provisioning station 400 may include a user interface 412 for displaying information relating to the programming of one or more tags or any other suitable information. The provisioning station 400 may additionally include an LED 414 associate with each station 404 to indicate a status of programming of the tag within the particular station 404 (e.g., the LED may be illuminated red or yellow during programming and/or green when programming is complete).

Figure 12:
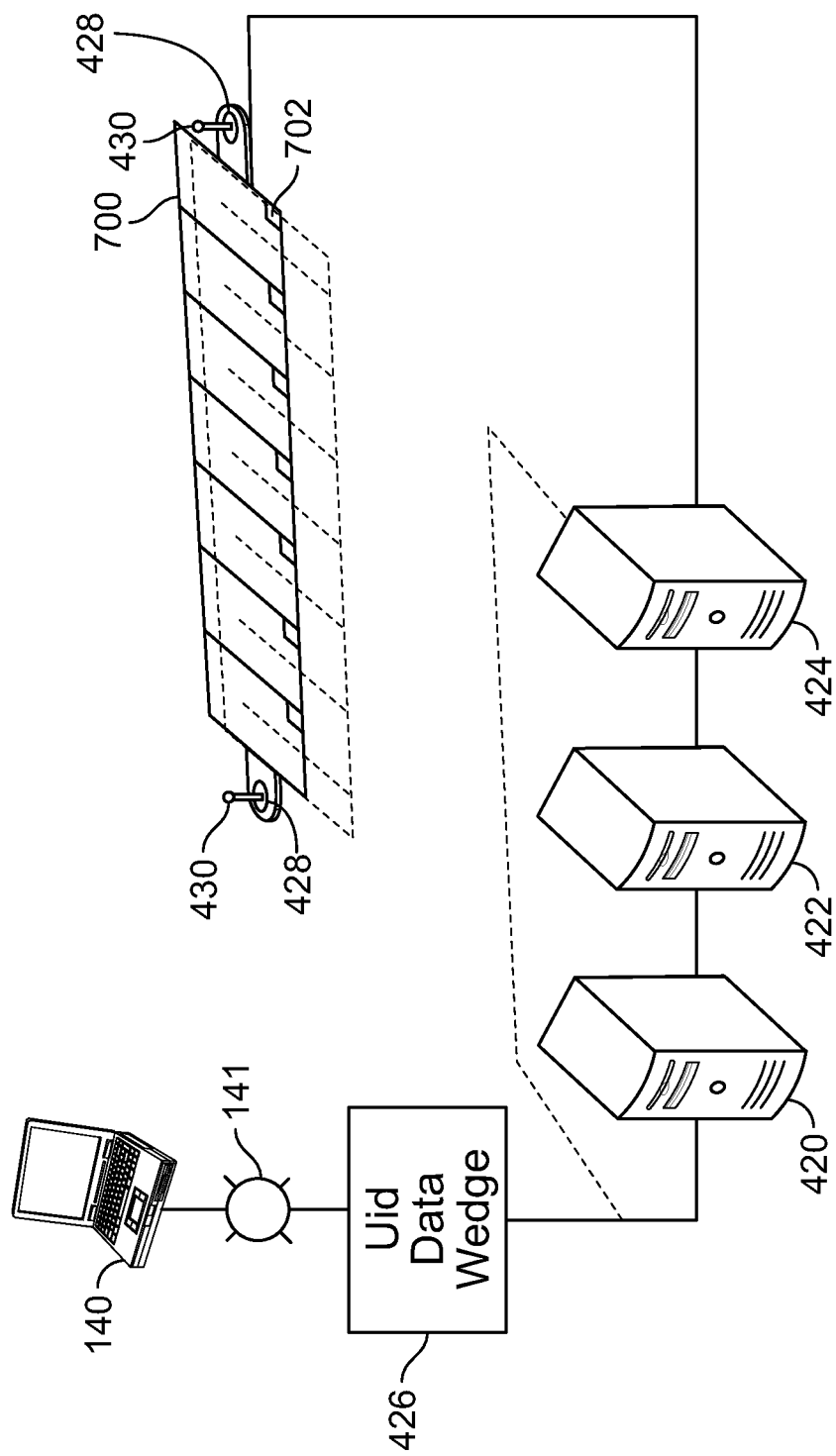
FIG. 12 is a schematic view depicting the components of the provisioning station of FIGS. 10 and 11.

Referring to FIG. 12, the provisioning station 400 includes the tag reader 410, a RFID reader/writer 422, multiplexer 424, and a communication port 420 connecting the RFID reader/writer 422 and the multiplexer 424. The multiplexer takes signals from the RFID reader/writer 422 and transmits it to different antennas associated with each of the stations 404. In some examples, the communication port 420, the RFID reader/writer 422, and the multiplexer 424 are disposed in an enclosure, for example, the housing 402. The tag reader 410 is in communication with a data wedge 426 via a communication link such as, for example, an Ethernet cable, ZigBee, and/or a Universal Serial Bus (USB). The data wedge 426 is an application that reads data, processes the data, and sends the data to the electronic platform 140 and/or the central server 141 of the data management system 130. In the illustrated example of FIG. 12, the tag reader 410 programs a plurality of tags 702 disposed on respective syringes 700. In the illustrated examples, the syringes 700 are enclosed in a sterile package, for example, a blister pack. In other examples, the package may comprise any other type of enclosure. The package of FIG. 2 includes two holes 428 to receive two pins 430, respectively, to secure the package adjacent the stations 404. The tag reader 410 programs the tags 702 disposed on the syringes 700 in succession while the syringes 700 are in enclosed in the package. While the foregoing exemplary embodiment details programming of tags 702 on syringes 700, such embodiment may be employed to program any tag.

Figure 13:
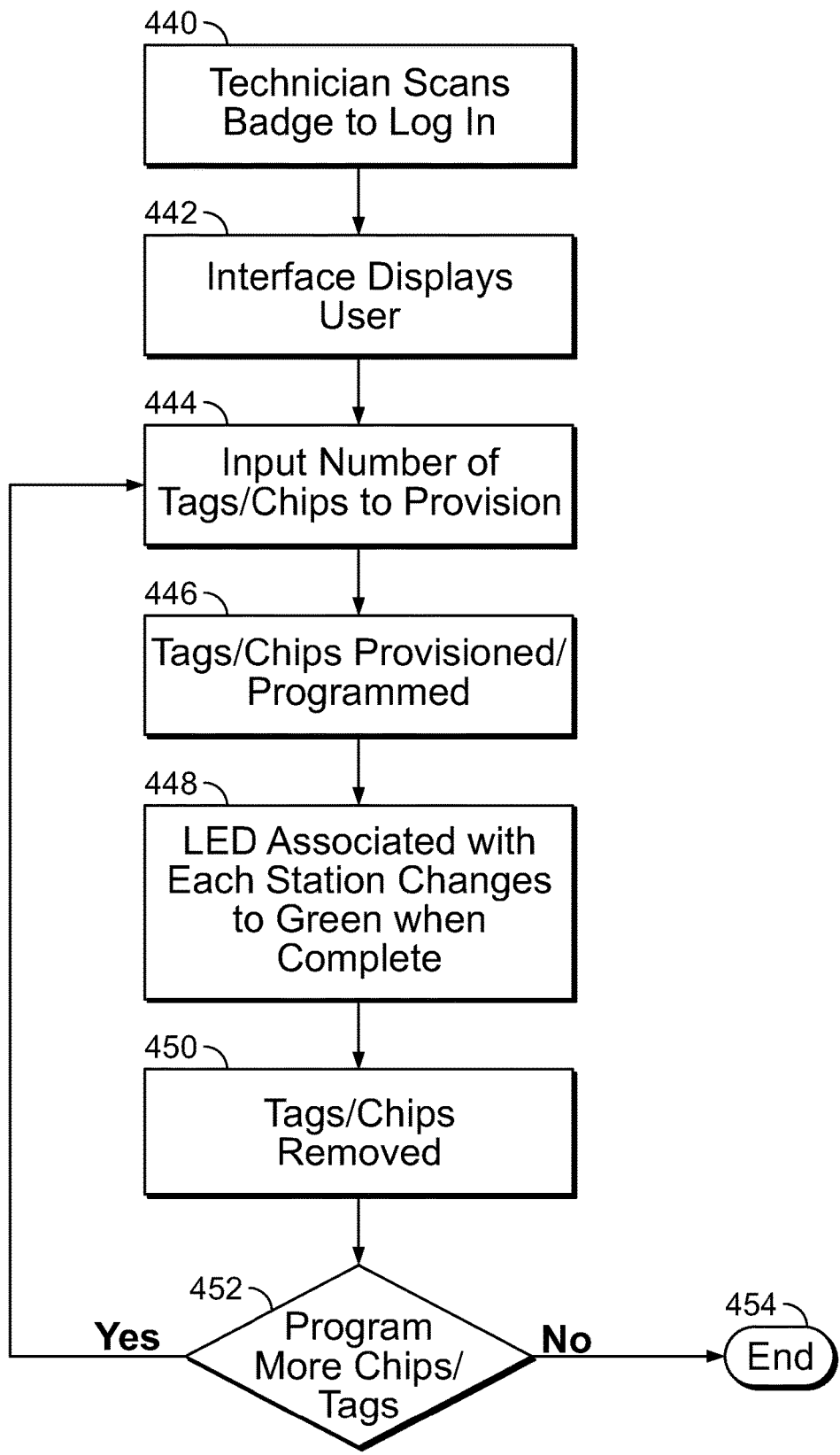
FIG. 13 is a flow chart depicting programming of one or more tags/chips utilizing the provisioning station of FIGS. 10-12.
Figure 14:
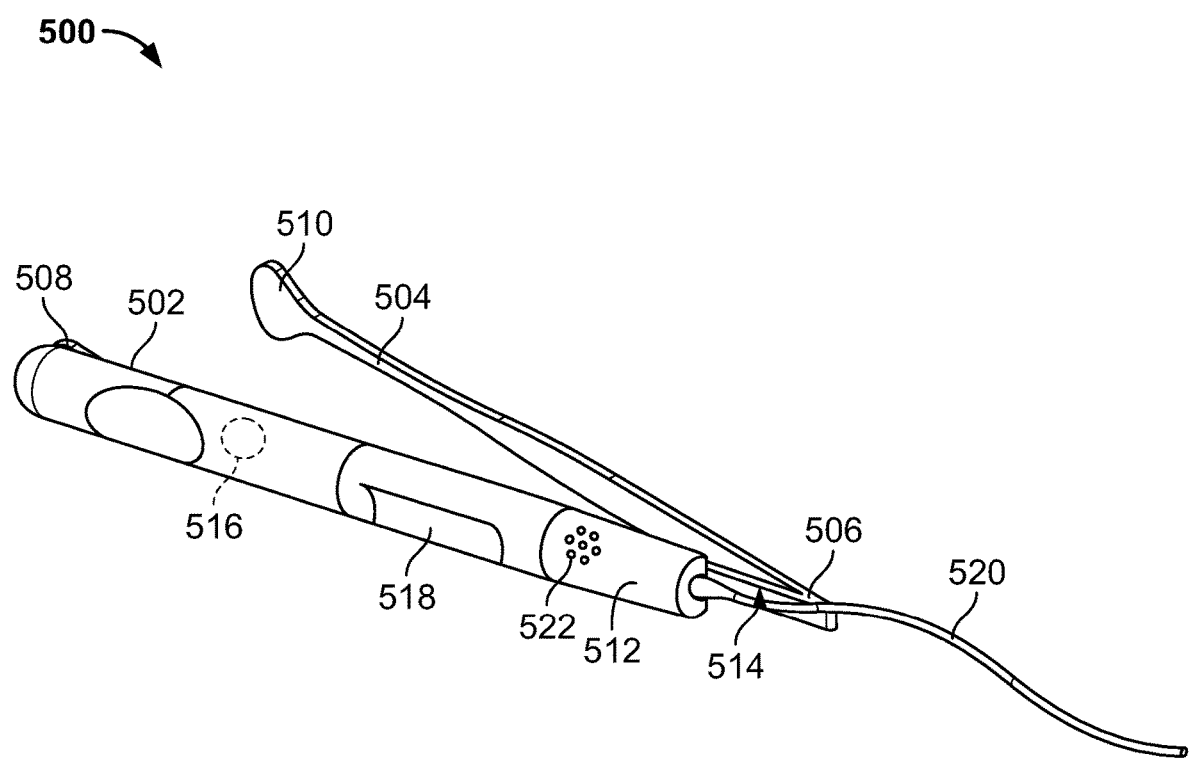
FIG. 14 is a perspective view of a pair of tongs for use within the research facility system of FIG. 1.

A method of programming a plurality of tags/chips utilizing the provisioning station 400 of FIGS. 10-12 is depicted in FIG. 13. In some embodiments, software may be implemented within a microprocessor or other controller of the provisioning station 400 to program tags. The technician may scan his or her badge at block 440 and information regarding the technician may be displayed on the user interface 412 at block 442. The technician would then be prompted to enter a number and order of tags for provisioning at block 444 at, for example, the user interface 412. Once a number and order of tags have been input and the tags are disposed within the stations 404, the provisioning station 400 verifies that tags are present in the identified stations 404 and the tags are programmed at block 446. During the programming step, the software tells RFID reader/writer 422 to write to the tag. When programming is complete, a color of the LED 414 associated with each of the stations 404 turns green at block 448 and the tags are removed at block 450. The provisioning station 400 may prompt the technician to program more chips at block 452. If the technician selects no, the process ends at block 454. If the technician selects yes, the process returns to block 444, wherein the technician again inputs a number of tags for provisioning.

Tags 170 are attached to animals 120 within the research facility 100 to provide easy and efficient identification of animals 120 and positive linking of the animals 120 with one or more laboratory objects, as will be discussed in greater detail below. For example, in a laboratory or other research setting, a technician may need to retrieve an animal 120. In doing so, the technician may use RFID capable tongs 500, as seen in FIG. 13, to retrieve, locate, and authenticate the animal 120. The tongs 500 generally include first and second arms 502, 504 connected at a hinge 506 and biased away from one another. The arms 502, 504 may be made of metal or any other suitable material. Each of the arms 502, 504 includes a gripper member 508, 510, respectively, at an end thereof to assist in grasping and picking up animals 120. A casing 512 is attached to an outer surface 514 of one of the arms 502, 504, for example, the first arm 502, as seen in FIG. 13. The casing 512 may include an RFID tag 516 that is capable of reading data or information from RFID chips or tags, for example, the tags 170 on animals 120 or other devices within the research facility 100. Other electronic circuitry may be disposed within the casing 512, as necessary. The casing 512 may further include a display 518, the function of which will be discussed in more detail below. A power cord 520 may extend from the casing 512 to provide power to the RFID tag 516 and/or any other electrical components within the casing 512. Optionally, the casing 512 may include a door for insertion and removal of one or more batteries for powering the tongs 500.

During use, the technician may use the tongs 500 to retrieve a specific animal 120 from, for example, the cage 106 of FIG. 1. In doing so, the technician inserts the tongs 500 into the cage 106 and grasps what he or she believes to be the correct animal 102 with the gripper members 508, 510. Upon grasping an animal 120, or as the animal 120 is being removed from the cage 106, the RFID tag 516 reads the information in the RFID tag 170 attached to the animal 120 and may display information relating to the animal 120, for example, the unique identification number identifying the animal 120 or any other information, on the display 518 and/or transmits the information to the data management system 130, for example, for display. In this manner, the technician does not need to fully remove the animal 120 from the cage 106 to know if he or she has obtained the correct animal 120. In other embodiments, a speaker 522 may be positioned within the casing 512 and the tongs 500 may include the appropriate electronic components to provide, upon grasping of an animal 120 or as the animal 120 is being removed from the cage 106, an audio signal indicating information relating to the animal 120. In exemplary embodiments, a number of digits (e.g., the last three digits) of the unique identification number of the animal 120 or any other audio signal may be utilized to indicate whether the correct animal 120 has been selected. In other embodiments, a visual indicator (e.g., an LED of differing colors) may be utilized to indicate whether the correct animal 120 has been selected. In other embodiments, the casing 512 may include a keypad or other input wherein a technician may be able to input, for example, the unique identification number of the animal 120. Upon grasping or removal of the animal 120, an audio or visual signal may be actuated to indicate whether the correct animal 120 has been selected. In an exemplary embodiment, the casing 512 may additionally include one or more light emitting diodes that change color based on animal selection (e.g., red upon incorrect selection and green upon correct selection). In still other embodiments, the data management system 130 may provide an audio or visual indicator at, for example, the electronic platform 140 or any other component of the system 130, that indicates whether the correct animal 120 has been selected and/or indicates information relating to the animal 120.

The features and components of the RFID capable tongs 500 of FIG. 13 may alternatively or additionally be utilized in conjunction with other laboratory objects for obtaining and holding animals 120, for example, a container, a net, or any other animal handling object.

After an animal 120 has been removed from the cage 106, any number of different actions may be taken with respect to the animal 120. One such action is taking a weight of the animal 120. An exemplary scale 600 for use in the system 100 of FIG. 1 is depicted in FIGS. 14-17. The scale 600 generally includes a base 602 having a top surface 604 on which a laboratory object or animal 120 is to be placed to weigh the laboratory object or animal 120. When, for example, a weight of an animal 120 is to be measured, the animal 120 is placed on the top surface 604 of the scale 600 (or in or on an accessory disposed on the top surface 604 of the scale 600 as described in greater detail below with reference to FIGS. 15-17). As will be discussed in more detail below, the technician may scan their badge 720 prior to the weight measure so that the system 100 knows the specific technician taking the measurements. The scale 600 measures the weight of the animal 120. In some examples, the scale 600 includes an RFID tag 607 that receives information related to the animal 120 by reading the tag 170 associated with the animal 120. In some examples, the scale 600 communicates the information related to the animal 120 (e.g., an identification number of the animal 120, one or more prior weights of the animal 120, and/or any other suitable information) and the current weight of the animal 120 to the data management system 130 (FIG. 1), which may store the information and the weight in the database 152 and/or 156. Thus, the weight of the animal 120 may be automatically stored in the database 152 and/or 156 when the current weight of the animal 120 is measured by the scale 600.

The exemplary scale 600 of FIGS. 13-17 includes a display 606, one or more of a visual indicator 608, a reset button 610, and USB, Ethernet, or other connections 612, and a sensor 616. In other examples, the scale 600 includes one or more additional and/or alternative features and/or components. The scale 600 may be battery operated, for example, by replaceable or rechargeable batteries, and/or may have a corded power supply. The display 606 may display messages such as, for example, scan warnings that provide a first color if the scale 600 is ready to weigh, a second color if weighing is in process, and a third color if the scale 600 is not ready, and/or one or more additional and/or alternative messages. In some examples, the display 606 displays information received from a tag (e.g., the tag 170 associated with the animal 120 or a tag associated with an laboratory object, a weight of an laboratory object or an animal 120 weighed via the scale, a name of an accessory (e.g., a cylinder or a bowl) to be disposed on the top surface 604 of the scale 600, and/or additional and/or alternative information). The visual indicators 608 of FIG. 13 may be light emitting diodes (LEDs). In other examples, the scale 600 includes one or more additional and/or alternative types of visual (or audio) indicators. In the illustrated example, the visual indicators 608 indicate a level of charge of batteries employed by the scale 600 and/or a type of wireless protocol employed by the scale 600 (e.g., Bluetooth™ Ethernet, Wi-Fi, etc.). The sensor 616 may be a motion, infrared, light, or other sensor that senses when an animal 120 or laboratory object is placed on the sale 600, which would activate the RFID tag 607 to read data from the RFID tag 170 on the animal 120 and begin the weighing process. The scale 600 may include a number of metal tabs 618 that may be in communication with an antenna integrated into a tray or accessory disposed on the scale 600, as discussed below.

Figure 15:
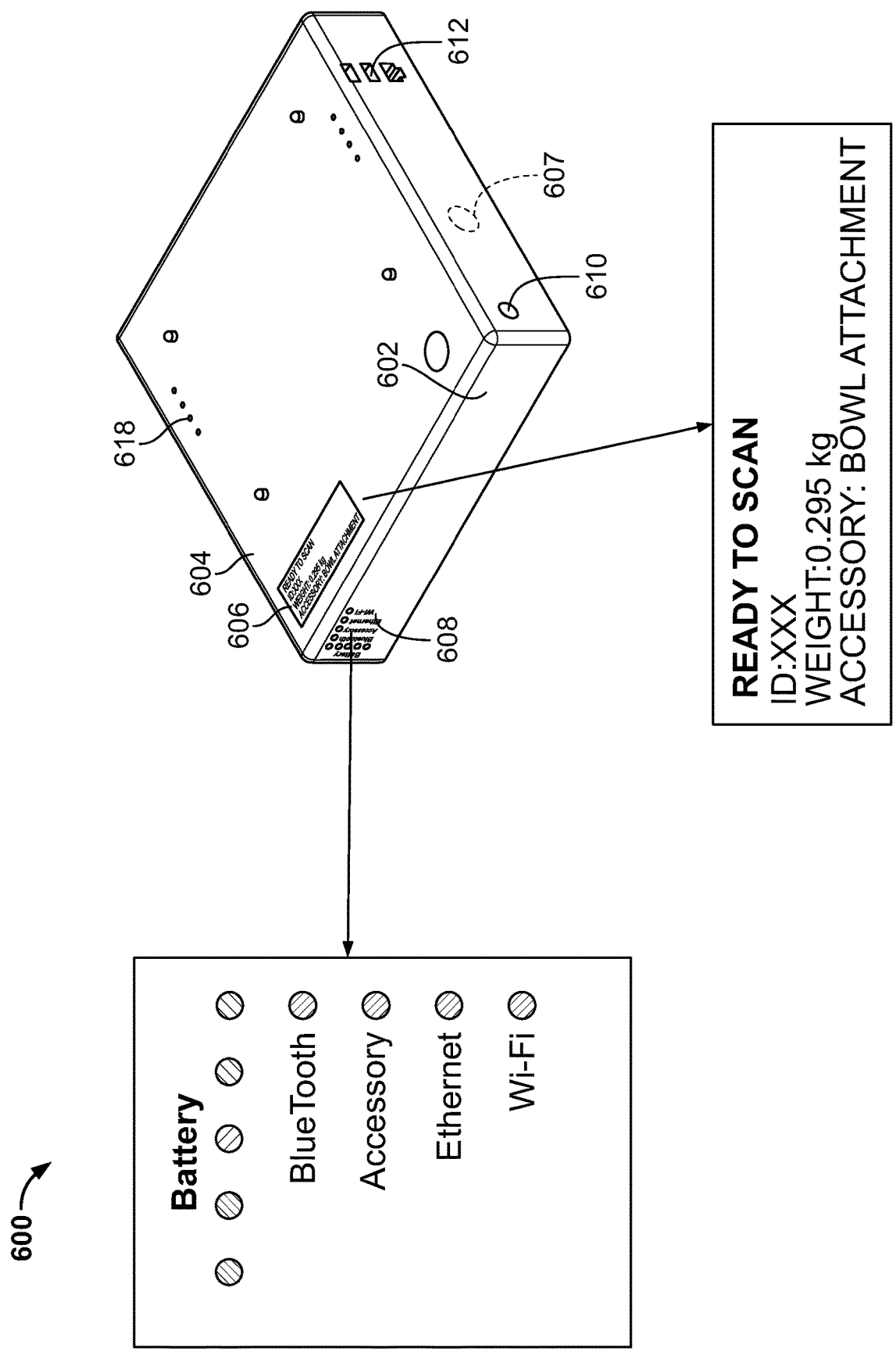
FIG. 15 is a top perspective view of a first embodiment of a scale for weighing animals or objects and for use within the research facility system of FIG. 1.
Figure 16:
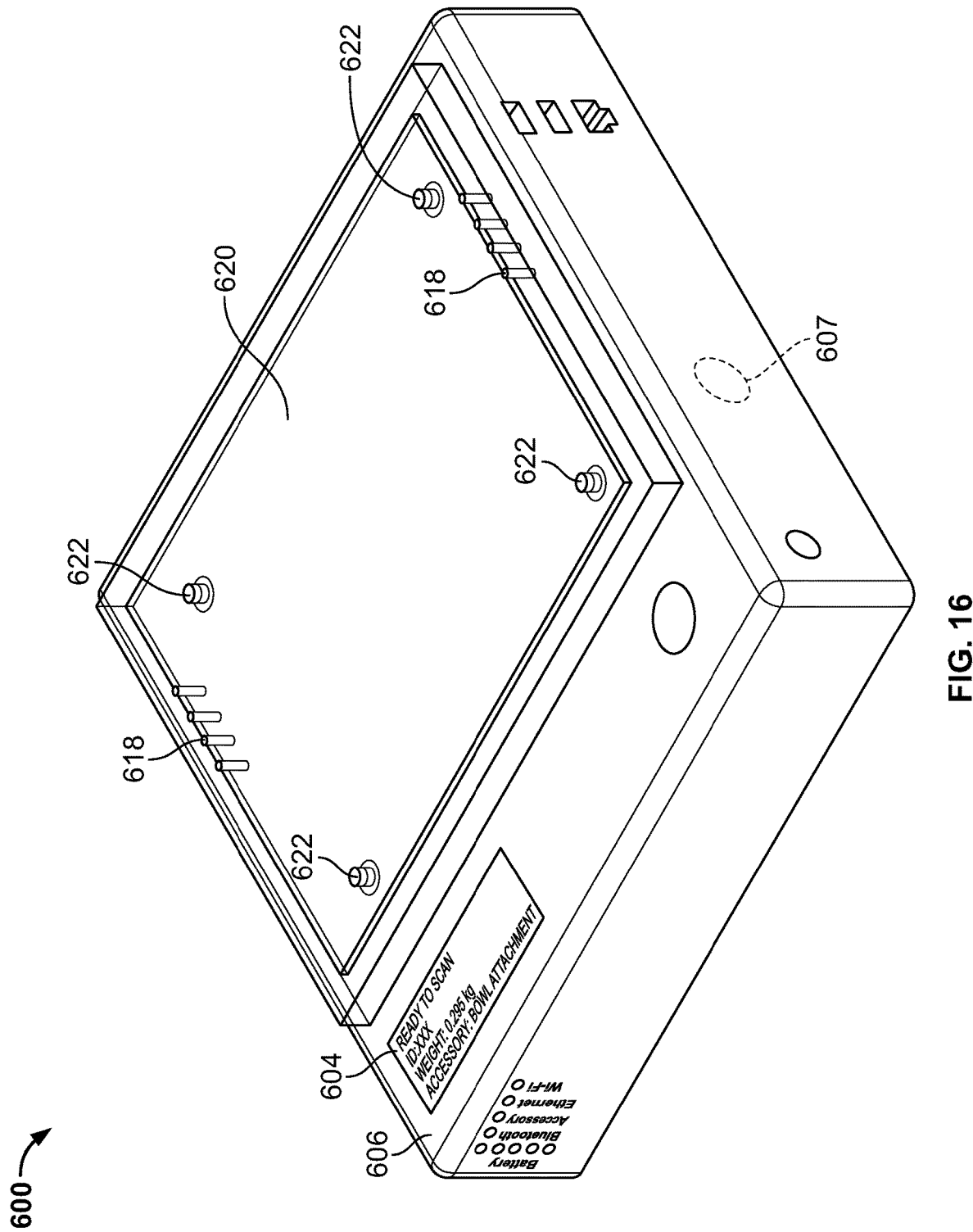
Figure 20:
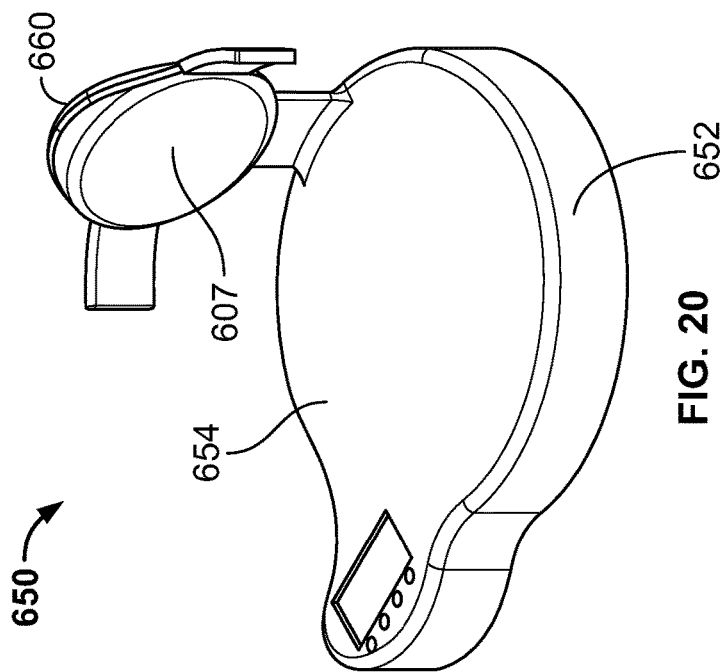
FIGS. 19 and 20 are top perspective views of alternate embodiments of a scale for weighting animals or objects and for use within the research facility system of FIG. 1.

Any number of accessories may be utilized with the scale 600. In an exemplary embodiment, a tray 620, as seen in FIG. 15, may be disposed on the top surface 604 of the scale 600 of FIG. 14. In the illustrated example, the top surface 604 of the scale 600 includes four pins 622 that are received in four receptacles (not shown), respectively, of the tray 600 to secure the tray 620 to the top surface 604. A hollow cylinder 630 is depicted in FIG. 16 as being supported by the tray 620. The cylinder 630 may confine an animal, a laboratory object, a liquid, or any other suitable item to be weighted on the scale. A bowl 632 is depicted in FIG. 17 as being supported by the tray 620. Similar to the cylinder 630, the bowl 632 may confine an animal, a laboratory object, a liquid, or any other suitable item to be weight on the scale. In other examples, one or more additional and/or alternative accessories may be supported on and/or coupled to the tray 620 and/or one or more additional and/or alternative portions of the scale 620. Any of the accessories may be attached to the scale 600, for example, the accessory may clip, twist, snap, friction fit, or screw onto the scale 600.

Figure 19:
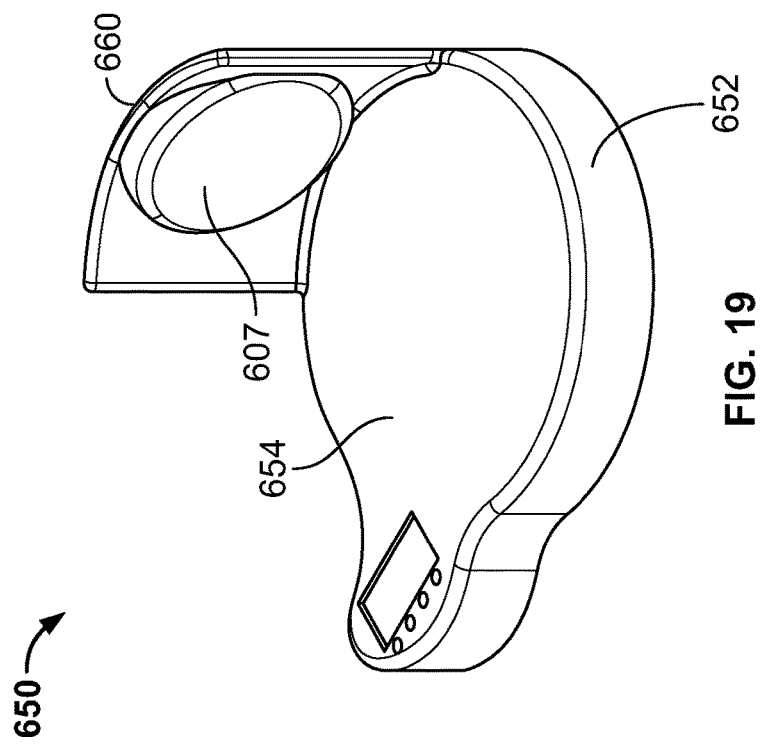

A further exemplary embodiment of a scale 650 is depicted in FIG. 18. The scale 650 generally includes a base 652 having a top surface 654 on which a laboratory object or animal 120 is to be placed to weigh the laboratory object or animal 120. The scale 650 of FIG. 18 may include any of the features or components and/or may function in the same manner as discussed in detail above with respect to the scale 600 of FIGS. 14-17. Another embodiment of a scale is shown in FIG. 19, which is similar to the scale 650 of FIG. 18, and will thus include the same reference numerals as FIG. 18. In the embodiments of FIGS. 18 and 19, the RFID tag 607 may be incorporated into a base of the scale or may be incorporated into an upstanding wall 660 to provide an uninterrupted path of communication.

Figure 21:
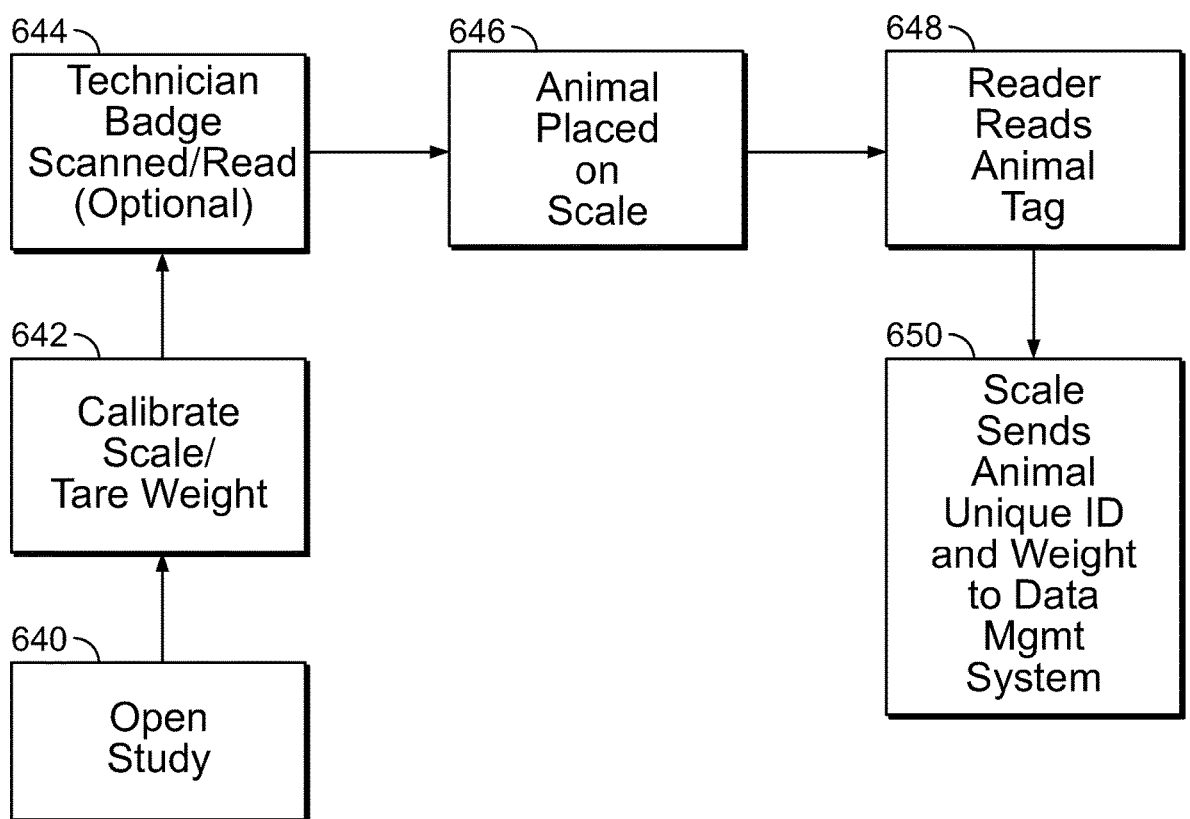
FIG. 21 is a flowchart depicting a process for tracking the weighing an animal in the systems disclosed herein.

During use of the scale 600, as seen in the flowchart of FIG. 21, the electronic platform 140, for example, in the form of a computer, is turned on and the desired study is opened up at block 640 utilizing a software program, as discussed in greater detail below. The scale 600 is calibrated, a cylinder 630, bowl 632, or other suitable container is placed on the scale 600, if utilized, and a tare weight of the container is taken at block 642. At block 644, the technician may optionally scan his or her badge. An animal 120 or laboratory object is thereafter removed from the cage 106 (or other container). In some embodiments, a wand (not shown) having an RFID tag is waved over the animal 120 to identify the animal 120, wherein the wand may include an antenna connected to an RFID reader/writer that reads information associated with the RFID tag. The wand may include a display that shows the unique identification number of the animal 120 (or laboratory object) or may in any other suitable manner indicate the unique identification number of the animal 120 and/or indicate whether the correct animal has been selected. If utilized, the wand may be dual frequency, for example, low frequency/ultra high frequency, low frequency/high frequency, high frequency/ultra high frequency, or any other dual frequency. The wand may be utilized at any point in time or in any location in the research facility system 100 to determine an identity of an animal or a laboratory object.

The animal 120 is then placed into the container on the scale 600 at block 646, the RFID tag 607 in the scale 600 reads data relating to the animal 120 (or laboratory object) at block 648, and, once the animal 120 (or laboratory object) has settled, the scale 600 determines a current weight of the animal 120 (or laboratory object) and automatically sends the weight and relevant data regarding the animal 120 or laboratory object to the data management system 130 (FIG. 1) at block 650. In some embodiments, the scale 600 includes a clock such that the scale 600 can record a time and/or a date on which the animal 120 or laboratory object was positioned on or near the scale and/or weighed via the scale 600 and communicates the time and/or the date to the data management system 130 with the weight and other relevant data regarding the animal 120 (or laboratory object). Optionally, the time and/or date may be extracted from control circuitry or a microprocessor in the scale 600 or from the data management system 130. In exemplary embodiments, the scale 600 may send the unique identification number for the animal 120 or laboratory object with the weight through any suitable wireless protocol to the data management system 130. Optionally, the scale 600 may include a wired connection to the data management system 130.

Other laboratory objects, such as medical devices, technician badges, vials, microscope slides, syringes, needles, tongs, or any other suitable objects, may be configured to communicate the with data management system 130. In an exemplary embodiment, a syringe or other dosing apparatus (e.g., a vial or other dosing apparatus) 700 includes an RFID tag 702 similar to the RFID tags 170 associated with animals 120. The RFID tag 702 receives, stores, and/or communicates information related to the syringe 700. For example, the RFID tag 702 may receive, store, and/or communicate information related to a drug to be injected via the syringe 700 (e.g., a dosage, a concentration, a name of the drug, etc.), a part number assigned to the syringe 700, an indication that the syringe 702 has dispensed the drug, and/or any other suitable additional and/or alternative information. In an exemplary embodiment, the RFID tag 702 may collect information from the RFID tag 170 of the animal 120 and transmit information related to syringe 700, information related to the animal 120, time and/or date of dosage, and any other relevant information to the data management system 130.

In exemplary embodiments, the RFID tag 702 of the syringe 700 may additionally communicate with the data management system 130 to, for example, receive information regarding an animal 120 (e.g., a unique identification number and/or other information). In some embodiments, the syringe 70 and/or the data management system 130 may compare the syringe identification number to a stored syringe identification number and, if the syringe identification number matches the stored syringe identification number, the electronic platform 140 and/or the syringe 700 may display an indication that the syringe 700 includes the drug that is to be injected into the animal 120. Still further, in some embodiments, the syringe and/or the data management system 130 may compare the animal identification number to the identification number of the animal 120 to be injected and, if the identification numbers match, the electronic platform 140 and/or the syringe 700 may display an indication that the animal 120 is or is not the correct animal 120 to be injected. The data management system 130 may, therefore, enable the technician to confirm that the animal 120 is or is not the correct animal 120 to be injected and the drug in the syringe 700 is or is not the proper drug to be injected into that particular animal 120. In some examples, when the drug is injected into the animal 120, the RFID tag 702 communicates a time and/or a date to the data management system 130 to log the time and/or the date when the animal 120 was injected with the drug.

Figure 22:
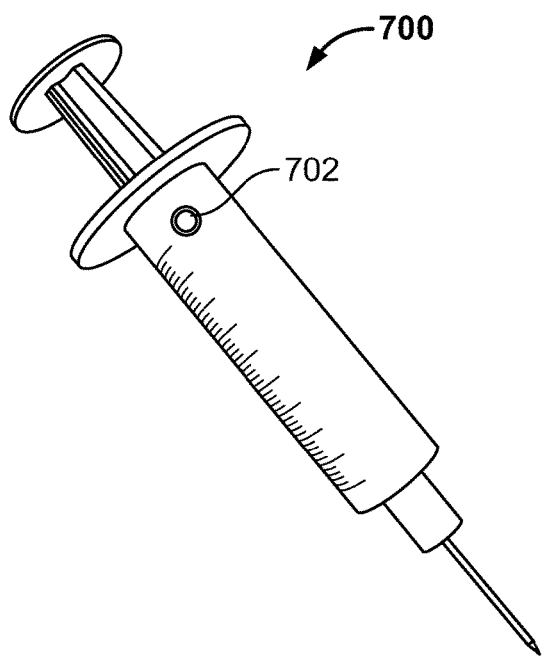
FIG. 22 is a perspective view of a dosing apparatus or use within the research facility system of FIG. 1.

A method of injecting an animal 170 utilizing the syringe or dosing apparatus 700 is depicted in FIG. 22. Before dosing, the technician may first optionally scan his or her badge at block 760, the tag 170 associated with the animal 120 is scanned at block 762, the syringe or dosing apparatus 700 is scanned at block 764, and the RFID tag 730 associated with the cage 106 is scanned at block 766, for example, using the tongs or the wand described above, a handheld reader, or any other suitable reader device. If the animal 120, syringe 700, and cage RFID tag 730 do not match (block 768), the process ends at block 770. If the animal 120, syringe 700, and cage RFID tag 730 match at block 768, the animal 120 is administered the medication at block 772 and data relevant to the animal 120 and the dosing is forwarded to the data management system 130 at block 774.

In another exemplary embodiment, as seen in FIG. 1, a technician badge 720 may include an RFID tag 722. The technician may carry the badge 720, for example, on and/or in a key fob, an access card, safety glasses, a lab coat, and/or any other equipment, clothing, or object carried, worn, or used by the technician. The tag 722 receives, stores, and/or communicates information related to the technician. For example, the tag 722 may receive, store, and/or communicate an identification (e.g., a name) of the technician, a position or title of the technician, a number (e.g., a unique identification number) assigned to the technician, the badge 722, or other equipment, clothing, or object employed to carry the tag 722, actions undertaken by the technician, and/or additional and/or alternative information.

The badge 720 may communicate the information stored on the badge 722 to other equipment in the research facility system 100, for example, the cage 106, the scale 600, the tongs 500, or any other laboratory object within the research facility 100 having an RFID tag. In this manner, when a technician undertakes any action within the research facility system 100, information stored on the badge 722 may be transmitted to an associated RFID tag. For example, when a technician approaches the cage 106, an RFID tag 730 associated with the cage 106 may record and/or transmit to the data management system 130 that the technician approached, opened, and/or removed something from the cage 106 and/or may further record and/or transmit information associated with the action taken, the technician, and the animal 120 or laboratory object associated with such action. In some embodiments, if the tongs 500 are utilized to remove the animal 120, the RFID tag 514 in the tongs 500 may record and/or transmit information associated with the badge 722 and/or the animal 120 to the data management system 130. Still further, if the animal 120 (or laboratory object) is placed on the scale 600 for weighing or any of the tags discussed herein are positioned and/or programmed within the provisioning station 400, the RFID tag 607 in the scale 600 or the RFID reader 410 in the provisioning station 400 may record and/or transmit information associated with the badge 722 and/or the animal 120 (or laboratory object) to the data management system 130. The badge 722 provides a view of who is performing what actions with respect to what animals 120 (or laboratory objects) throughout the research facility system 100.

As noted above, each cage 106 may include an RFID tag 730. In some embodiments, each cage 106 and/or rack 104 may include RFID tags 730, 732 for tracking location of the cage 106 or rack 104, actions undertaken within or around the cage 106 or rack 104, and/or any other suitable information related to the cage 106 or rack 104 and/or communication information to the data management system 130 and/or other RFID tags within the system 100. In some embodiments, one or both of the RFID tags 730, 732 may be configured to track, store, and/or communicate information related to sanitation of the cage 106 and/or rack 104. As seen in FIG. 1, a washing station 800 associated with the research facility system 100 may include an RFID tag 802, which communicates with the RFID tags 730, 732, the technician badge 722, and/or any other tags within the system 100 to transmit data relating to sanitization of the cage 106 and/or rack 104, for example, a time and date, actions taken, etc.

Figure 23:
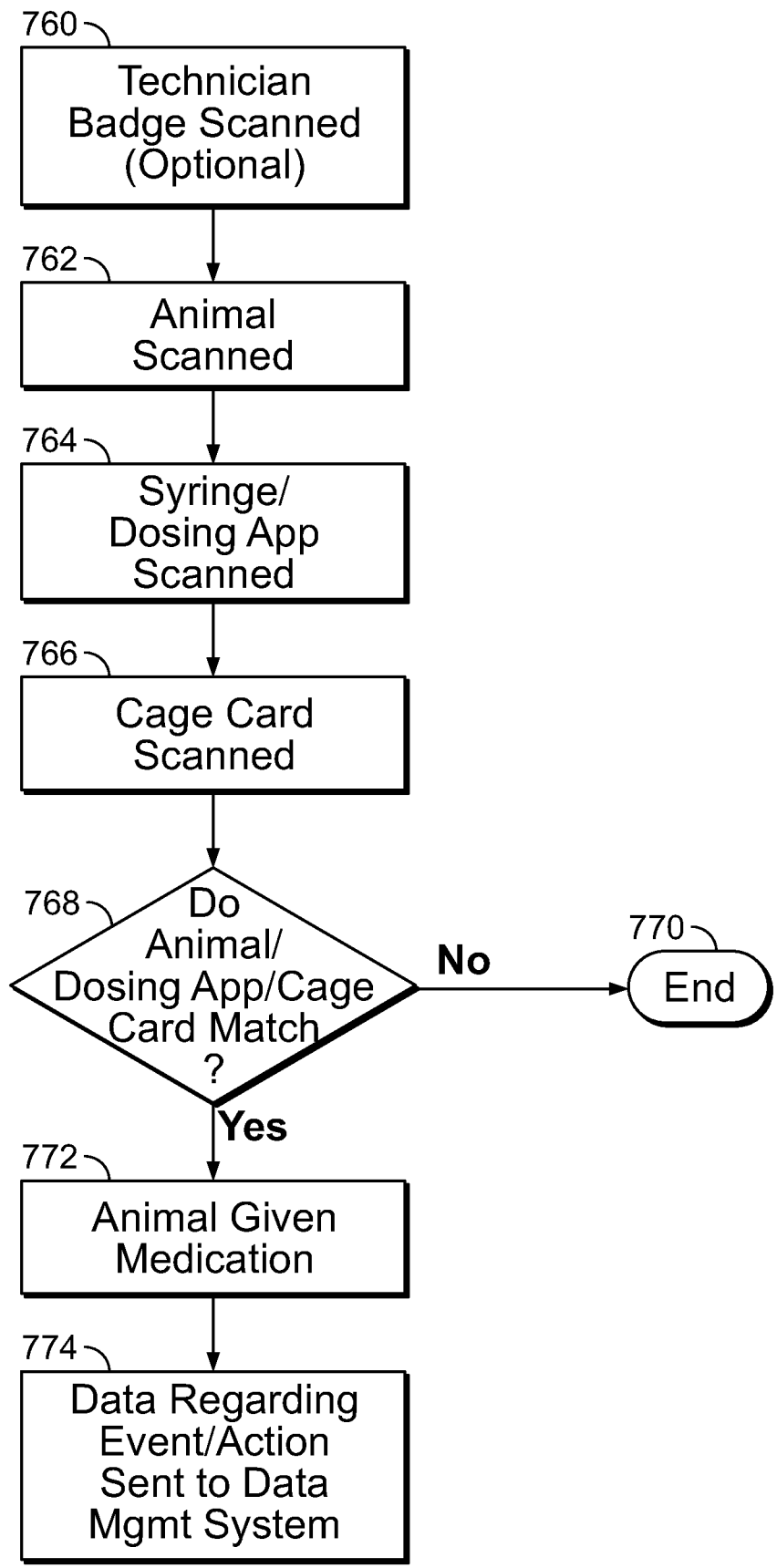
FIG. 23 is a flowchart depicting a process for tracking the dosage of an animal with a drug in the systems disclosed herein.
Figure 24:
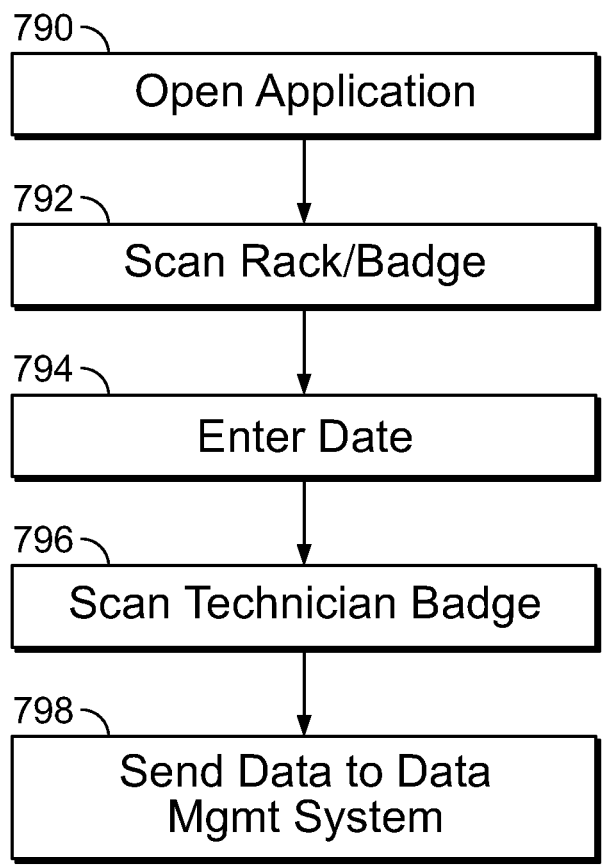
FIG. 24 is a flowchart depicting a process for tracking the sanitization of a rack or cage in the systems disclosed herein.

A flowchart illustrating a process for tracking sanitization of a rack 104 and/or cage 106 is depicted in FIG. 23. The technician opens a software application 820 on an electronic platform 140, for example, a mobile device at block 790. The rack 104 and/or cage 106 is scanned at block 792, a date of sanitization is entered into the application 820 at block 794, and the badge 720 of the technician is scanned at block 796. Data relative to the sanitization is thereafter forwarded to the data management system 130 at block 798.

Referring again to FIG. 1, in the illustrated example, the technician (or other research facility employee) employs the electronic platform 140, for example, a smart phone, a tablet, a laptop, and/or any other suitable device. The electronic platform 140 may include the application 820 in the form of a software program operated by the CPU 150, an application, a web-based program, and/or any other suitable application. The software application 820, when accessed through the electronic platform 140, can access data either on the electronic platform 140 or through communication with the central server 141, as discussed in detail above. The software application 820 may include any number of features and functions, but overall, integrates various actions (e.g., removing or replacing of animals, dosing of drugs, weighing of animals, sanitizing of cages 106 and/or racks 104, etc.) taken within the research facility system 100, various animals 120 within the research facility system 100, various laboratory objects (e.g., scales, syringes, cages, etc.) within the research facility system 100, and technicians within the research facility system 100. In this manner, the software application 820 receives, analyzes, and/or displays information related to all aspects of the research facility system 100.

The software application 820 may work in conjunction with a scanning apparatus, for example, on the electronic platform 140. One or more of the laboratory objects and/or animals within the research facility 100 may include a barcode, RFID tag, or other device capable of scanning with the scanning apparatus to record information related to the particular laboratory object, animal, or technician within the research facility system 100.

In an exemplary embodiment, the software application 820 may include a study protocol that includes various actions to be taken throughout the research facility system 100 with respect to various animals 120 and/or laboratory objects. The software application 820 may be accessed on the electronic platform 140 to undertake any number of these actions. In a specific non-limiting example, a technician may need to inject an animal 120 with a dosage of a drug using a syringe 700, take blood from the animal 120 and place it in a vial that is labeled, and take a weight of the animal 120 utilizing the scale 600. Before undertaking any actions, the technician may scan one or more of his or her badge 720, the RFID tag 730 on the cage 106 associated with the animal 120, the RFID tag 170 associated with the animal 120, the RFID tag 702 associated with the syringe 702, the vial, the label for placement on the vial, and/or the RFID tag 607 associated with the scale 600. During this process, positive linking of the various laboratory objects (i.e., badge, cage, animal, vial, etc.), the animal 120, and the actions to be undertaken occurs. More particularly, the software application 820 verifies that the proper laboratory objects are being utilized for that particular animal 120, that the actions are being undertaken on the proper day and at the proper time, and that the laboratory objects are, in fact, the correct laboratory objects for use on the particular animal 120. The software application 820 may include any number of alerts to indicate, for example, the wrong animal 120 and/or laboratory object(s) has been selected, the action(s) is being undertaken at the wrong time or on the wrong day, etc. The software application 820 may allow the action(s) to be undertaken if the correct animal 120 and/or laboratory object(s) are selected or may prompt the technician that he or she should not proceed if a correct animal 120 or laboratory object has not been selected. In this manner, the technician is forced to adhere to the study protocol to render more accurate study results.

In some embodiments, some of the laboratory objects may include a tag that uses a first communication protocol, for example, RFID technology, and other laboratory objects may include a tag that uses a second communication protocol, for example, barcode technology. In the example immediately above, the tags 170, 607, 702 associated with the animal 120, the scale 600, and the syringe 700, respectively, may use RFID technology to communicate and tags associated with, for example, the vial, the label, etc. may use barcode technology.

At any given point in time, the software application 820 can provide real-time data regarding how many animals are in the facility, where the animals are located, what drugs have been administered to what animals and when, weights of the animals, what technicians have performed what actions and when, and various other data relating to operation of the research facility 100.

The data management system 130 may additionally provide for billing, for example, per cage 106 by a specified period of time (e.g., day or week). A cage 106 or rack 104 may be scanned, thereby generating a full report of the animals 120 within the particular cage 106 or rack 104 and providing updated costs related to the selected cage 106 or rack 104.

Communication within the research facility system 100, for example, between the data management system 130, the animals, and the various laboratory objects (e.g., racks 104, cages 106, scales 600, syringes 700, badges 720, etc.), may be by means of Bluetooth, zibee, Wifi, or any other wireless communication protocol.

While certain examples have been disclosed above, the claims are not limited thereto, and numerous other examples may fall into the scope of the claims. The entire disclosure of each patent and publication cited herein is incorporated by reference, as if each such patent or publication were individually incorporated by reference herein.

The invention claimed is:

1. A computerized identification and protocol prescription system for an animal research facility, the system comprising:
   a plurality of scanning devices;
   a plurality of detection tags, wherein a detection tag is respectively associated with each of 1) at least one animal; 2) at least one laboratory object; and 3) at least one laboratory technician, wherein each of the plurality of detection tags is configured to be detected by one of the plurality of scanning devices based upon proximity between a said scanning device and a said detection tag; and a data management system having a computer processor coupled to each of the plurality of scanning devices, the data management system configured to:
  detect by the one of the plurality of scanning devices one or more animal detection tags and at least one laboratory object and at least one laboratory technician;
  correlate, based upon prescribed rules, one or more animal detection tags with at least one laboratory object and at least one laboratory technician when an animal is located in predetermined proximity to predetermined detection tags respectively associated with each of the at least one laboratory object and laboratory technician;
  prescribe a study protocol for an animal when one or more animal detection tags is correlated, without user intervention, with the at least one laboratory object and at least one laboratory technician, wherein the prescribed study protocol consists of one or more research actions to be taken utilizing the prescribed laboratory object and laboratory personal with respect to the animal having the detection tag determined to be located in predetermined proximity to the predetermined detection tags respectively associated with each of the laboratory object and laboratory technician, wherein the one or more research actions includes generating labelling information, when one or more animal detection tags is correlated, without user intervention, with the at least one laboratory object and at least one laboratory technician, for a vial to contain blood drawn from an animal correlated with the least one laboratory object and at least one laboratory technician.

2. The system of claim 1, wherein at least an animal detection tag and the technician detection tag are radio-frequency identification (RFID) tags.

3. The system of claim 1, wherein the laboratory object is selected from the group consisting of: a vial, a dosing apparatus, a scale, a cage, a rack, a container, a label, or a microscope slide.

4. The system of claim 1, wherein the data management system comprises at least one electronic platform for receiving and displaying information from the animal, technician and laboratory object detection tags.

5. The system of claim 4, wherein the data management system further comprises a central server in communication with the at least one electronic platform over a wireless data network for transmitting information between the at least one electronic platform and the central server.

6. The system of claim 1, wherein the animals are mice or rats.

7. The system as recited in claim 1, wherein the study protocol includes a drug dosage to be injected in an animal.

8. The system as recited in claim 1, wherein the study protocol includes identification of a time of day a procedure is to be conducted on an animal.

9. The system as recited in claim 1, wherein the study protocol includes alerts of improper actions regarding a certain animal procedure to be undertaken.

10. The system as recited in claim 9, wherein the alerts include identification of an improper animal to be subject for a certain animal procedure to be undertaken.

11. The system as recited in claim 9, wherein the alerts include identification of an improper laboratory object contemplated for use for a certain animal procedure to be undertaken.

12. The system as recited in claim 9, wherein the alerts include identification of an improper time of day contemplated for a certain animal procedure to be undertaken.

* * * * *